United States Patent
Bradbury et al.

(10) Patent No.: US 11,666,411 B2
(45) Date of Patent: Jun. 6, 2023

(54) SYSTEMS FOR AUGMENTED REALITY SURGICAL AND CLINICAL VISUALIZATION

(71) Applicant: Memorial Sloan Kettering Cancer Center, New York, NY (US)

(72) Inventors: Michelle S. Bradbury, New York, NY (US); Krishna Juluru, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 17/049,457

(22) PCT Filed: May 10, 2019

(86) PCT No.: PCT/US2019/031828
§ 371 (c)(1),
(2) Date: Oct. 21, 2020

(87) PCT Pub. No.: WO2019/217893
PCT Pub. Date: Nov. 14, 2019

(65) Prior Publication Data
US 2021/0045838 A1      Feb. 18, 2021

Related U.S. Application Data

(60) Provisional application No. 62/669,837, filed on May 10, 2018.

(51) Int. Cl.
*A61B 90/00* (2016.01)
*G06T 19/00* (2011.01)
(Continued)

(52) U.S. Cl.
CPC ............ *A61B 90/37* (2016.02); *A61B 90/361* (2016.02); *G06T 19/006* (2013.01);
(Continued)

(58) Field of Classification Search
CPC ...................................................... A61B 90/37
(Continued)

(56) References Cited

U.S. PATENT DOCUMENTS

| 8,084,001 B2 | 12/2011 | Burns et al. |
| 8,298,677 B2 | 10/2012 | Wiesner et al. |

(Continued)

FOREIGN PATENT DOCUMENTS

| AU | 2003247336 A1 * | 10/2003 | .......... A61B 5/0091 |
| EP | 3165153 A1 | 5/2017 | |

(Continued)

OTHER PUBLICATIONS

International Search Report, International Application No. PCT/US2019/031828 (Systems for Augmented Reality Surgical and Clinical Visualization, filed May 10, 2019), issued by ISA/European Patent Office, 5 pages, dated Aug. 19, 2019.

(Continued)

*Primary Examiner* — Javid A Amini
(74) *Attorney, Agent, or Firm* — Choate, Hall & Stewart LLP; William R. Haulbrook; Margo R. Monroe

(57) ABSTRACT

Presented herein are systems, methods, and architectures related to augmented reality (AR) surgical visualization of one or more dual-modality probe species in tissue. As described herein, near infrared (NIR) images are detected and rendered in real time. The NIR images are registered and/or overlaid with one or more radiological images (e.g., which were obtained preoperatively/perioperatively) by a processor [e.g., that uses an artificial neural network (ANN) or convolutional neural network (CNN) reconstruction algorithm] to produce a real-time AR overlay (3D representation). The AR overlay is displayed to a surgeon in real time. Additionally, a dynamic motion tracker tracks the location of fiducial tracking sensors on/in/about the subject, and this (Continued)

information is also used by the processor in producing (e.g., positionally adjusting) the AR overlay. The real-time AR overlay can improve surgery outcomes, for example, by providing additional real-time information about a surgical site via an intuitive visual interface.

20 Claims, 6 Drawing Sheets

(51) Int. Cl.
    *A61B 90/50* (2016.01)
    *H04N 5/33* (2023.01)

(52) U.S. Cl.
    CPC ... *A61B 2090/365* (2016.02); *A61B 2090/392* (2016.02); *A61B 2090/3979* (2016.02); *A61B 2090/502* (2016.02); *G06T 2210/41* (2013.01); *H04N 5/33* (2013.01)

(58) Field of Classification Search
    USPC .......................................................... 345/419
    See application file for complete search history.

(56) References Cited

U.S. PATENT DOCUMENTS

| | | | |
|---|---|---|---|
| 8,409,876 B2* | 4/2013 | Wiesner | A61P 35/00 436/524 |
| 8,961,825 B2 | 2/2015 | Wiesner et al. | |
| 9,122,054 B2* | 9/2015 | Osterhout | G02B 27/0172 |
| 9,625,456 B2 | 4/2017 | Bradbury et al. | |
| 10,359,916 B2* | 7/2019 | Masumoto | G06T 19/006 |
| 2003/0100824 A1* | 5/2003 | Warren | B33Y 30/00 600/407 |
| 2015/0366995 A1 | 12/2015 | Wiesner et al. | |
| 2016/0018404 A1 | 1/2016 | Iyer et al. | |
| 2017/0099479 A1* | 4/2017 | Browd | H04N 13/156 |
| 2017/0231714 A1* | 8/2017 | Kosmecki | A61B 90/37 345/419 |
| 2018/0133346 A1 | 5/2018 | Wiesner et al. | |
| 2019/0059736 A1* | 2/2019 | Maier-Hein | A61M 5/19 |
| 2020/0355614 A1* | 11/2020 | Sun | G06T 7/149 |

FOREIGN PATENT DOCUMENTS

| | | |
|---|---|---|
| WO | WO-2015/103420 A1 | 7/2015 |
| WO | WO-2015/179446 A1 | 11/2015 |
| WO | WO-2016/100340 A1 | 6/2016 |
| WO | WO-2016/179260 A1 | 11/2016 |
| WO | WO-2017/106525 A1 | 6/2017 |
| WO | WO-2017/189961 A1 | 11/2017 |
| WO | WO-2018/009379 A1 | 1/2018 |
| WO | WO-2018/102372 A1 | 6/2018 |

OTHER PUBLICATIONS

Written Opinion, International Application No. PCT/US2019/031828 (Systems for Augmented Reality Surgical and Clinical Visualization, filed May 10, 2019), issued by ISA/European Patent Office, 9 pages, dated Aug. 19, 2019.

\* cited by examiner

SYSTEMS FOR AUGMENTED REALITY SURGICAL AND CLINICAL VISUALIZATION

CROSS-REFERENCE TO RELATED APPLICATION

This application claims the benefit of U.S. Application Ser. No. 62/669,837 filed on May 10, 2018, the disclosure of which is hereby incorporated by reference in its entirety.

FIELD

This invention relates generally to systems and methods for augmented reality visualization of a subject in an operating room or other medical environment. In particular, this disclosure relates, in certain embodiments, to the visualization of a dual-modality probe species administered to a subject to improve the outcome of a medical procedure (e.g., a surgical procedure).

SUMMARY

Presented herein are systems, methods, and architectures related to augmented reality (AR) surgical visualization of one or more dual-modality probe species in tissue. In certain embodiments, NIR images are detected and rendered in real time, e.g., during surgery, in a clinical setting, and/or in a post-operative setting, e.g., to assist radiotherapy, e.g., by locating where radiotherapy should be applied. The NIR images are registered and/or overlaid with one or more radiological images (e.g., PET, SPECT, PET/CT, and/or SPECT/CT images which were obtained preoperatively/perioperatively) by a processor [e.g., that uses an artificial neural network (ANN) or convolutional neural network (CNN) reconstruction algorithm] to produce a real-time AR overlay (3D representation). The AR overlay is displayed to a surgeon (or other medical service provider) in real time. Additionally, a dynamic motion tracker tracks the location of fiducial tracking sensors on/in/about the subject, and this information is also used by the processor in producing (e.g., positionally adjusting) the AR overlay. The real-time AR overlay can improve surgery outcomes, for example, by providing additional real-time information about a surgical site (e.g., related to tissue and other anatomical structures beneath the skin of the subject that is otherwise not viewable) via an intuitive visual interface.

The radiological images show emission of the radiolabel(s) of the multimodal probe, while the NIR images show emission of the fluorophore of the multimodal probe. The radiological images may additionally show anatomical information (e.g., PET/CT or SPECT/CT images). An RGB video stream may additionally be used by the processor in producing the real-time AR overlay. In some embodiments, the AR overlay is rendered for viewing by the surgeon via a hands-free wearable device which has tracking sensors detected by the dynamic motion tracker. In some embodiments, the AR overlay is simply rendered on a display screen.

In some embodiments, (i) NIR images are detected in real time (not necessarily rendered for display), (ii) the processor uses the NIR images along with the radiological image(s) to produce a real-time AR overlay (e.g., where the NIR image(s) are used to orient/align the radiological images), and (iii) the AR overlay is displayed to the surgeon in real time.

In some embodiments, (i) a dynamic motion tracker tracks the location of fiducials on/in/about the subject, and (ii) the processor produces an AR overlay using the radiological images and the tracked location of the fiducials. Here, the fluorescent light emitted by the multimodal probe may simply be being viewed by the naked eye and may not require enhancement.

In some embodiments, (i) multispectral (e.g., hyperspectral) intrinsic tissue signals are detected by the NIR imaging apparatus (e.g., hyperspectral data acquisition device) and 3D functional information is derived [e.g., oxygenation states, e.g., perfusion (e.g., flow) status, e.g., determined voxel-by-voxel, or segmented volume by segmented volume], (ii) a dynamic motion tracker tracks the location of fiducials on/in/about the subject, and (iii) the processor produces an AR overlay using the tracked location of the fiducials and the detected intrinsic tissue signals (and/or the 3D functional information derived from the intrinsic tissue signals).

In certain embodiments, the systems enable a guided surgical approach for the pre-surgical and/or intraoperative planning phases of a surgical procedure. The systems and methods can also be used for planning and/or guiding other treatments (e.g., radiation therapy) administered in a clinical setting or a post-operative setting. A probe species (e.g., a dual-modality probe species), for example, a PET-optical ultrasmall silica nanoparticle imaging probe, facilitates this approach. Pre-operative radiographic techniques (i.e., computerized tomography, positron emission tomography) are employed, e.g., following administration of a dual-modality cancer-targeting PET-optical particle probe and placement of fiducial markers at strategic locations on the patient for tracking (the markers to stay in place during the surgical procedure). The technique involves acquisition of high-resolution volumetric imaging with virtual 3D reconstruction computed (e.g., employing machine learning techniques) and updated for real-time rendering. The virtual reconstructions are projected as an augmented reality (AR) overlay that is projected onto an image of the patient space and/or into a surgeon's field of view (e.g., via a headset viewer). The system interactively guides the surgeon to sites of disease specifically identified by the particles or other aspects of treatment management.

In certain embodiments, the systems allow a surgeon to assess the extent of malignancy and completeness of surgical excision while limiting the amount of normal tissue dissection using the optical component of C' dots. Upon exposure of the operative bed, real-time optical imaging acquisition strategies are combined with AR. A fluorescent diseased and/or normal tissue signal can be projected onto the patient space (e.g., virtually, via an AR overlay). The system may allow a surgeon to verify complete resection of disease, limit damage to normal vital tissue structures (i.e., nerves, glands), and permit real-time surgical decision-making.

For example, the system may allow localization of sentinel and distal lymph nodes to determine the best surgical route of entry and subsequently improve surgical-patient outcomes (i.e., less dissection, reduced/absence of complications, decreased morbidity, less time under general anesthesia). In certain embodiments, the system may ensure complete surgical resection of a tumor based on more accurately mapping surgical margins in relation to surrounding normal tissues and/or identifying residual disease at the operative site. The system may also allow visualization of normal vital tissue structures to minimize risk of injury or damage during surgical procedures. In certain embodiments, the systems facilitate pen-operative localization of metastatic disease sites.

In some embodiments, the described systems and methods are used for a clinical procedure rather than a procedure conducted in an operating room.

In one aspect, the invention is directed to a system for the rendering and real-time display of an augmented reality overlay representation of one or more dual-modality probe species in tissue for enhanced real-time visualization of one or more tissue structures of a subject (e.g., for intraoperative, perioperative, and/or preoperative imaging), the system comprising: a real-time NIR imaging apparatus (e.g., camera) for detecting near-infrared light at each of one or more discrete wavelengths each corresponding to an emission frequency of each of the one or more dual-modality probe species, said one or more probe species having been administered to the subject for accumulation in and/or about the one or more tissue structures for which visualization is to be enhanced (e.g., lymph node, nerve tissue, tumor tissue, etc.); a processor and a memory having instructions stored thereon, wherein the instructions, when executed by the processor, cause the processor to: receive and/or store one or more radiological images representing emission of one or more radiolabel species of the administered one or more dual-modality probe species (e.g., PET, SPECT, PET/CT, SPECT/CT, etc.); receive and/or store one or more series of NIR images (e.g., one or more video streams) obtained by the real-time NIR imaging apparatus, each series corresponding to an emission frequency of one of the one or more dual-modality probe species; and produce the real-time augmented reality (AR) overlay (e.g., 3D representation) using the one or more radiological images and the one or more series of NIR images (e.g., by performing an ANN/CNN reconstruction).

In certain embodiments, each of the one or more dual-modality probe species comprises a multifunctional nanoparticle species or other probe comprising one or more radiolabels and one or more fluorophores.

In certain embodiments, each of the one or more discrete wavelengths are within a range from 400 nm to 2500 nm, e.g., each of the one or more discrete wavelengths within NIR I (400-900 nm) and/or each of the one or more discrete wavelengths within NIR II (900-1700).

In certain embodiments, the one or more radiological images comprises one or more "still" 3D images or a time-series of 3D images, e.g., a sequence of 3D images obtained over a period of time.

In certain embodiments, the system further comprises a dynamic motion tracker for detecting tracking sensors and for producing real-time sensor position information, wherein the instructions, when executed by the processor, cause the processor to produce the real-time AR overlay using the one or more radiological images, the one or more series of NIR images, and the real-time sensor position information, and wherein the instructions, when executed by the processor, cause the processor to render the AR overlay for display (e.g., to a surgeon, e.g., via a hands-free wearable device with tracking sensors), and to update the real-time AR overlay in real-time (e.g., during a surgical procedure, e.g., for assisting radiotherapy (e.g., for locating where radiotherapy should be applied), e.g., according to movement of the subject, movement of the hands-free wearable device, and/or real-time evolution of the NIR images detected by the NIR imaging apparatus).

In certain embodiments, the sensors are placed on/in/around the subject and/or the sensors are placed on a hands-free wearable device.

In certain embodiments, the system further comprises an electronic display (e.g., the hands-free wearable device) for display of the AR overlay superimposed on a view of the subject.

In certain embodiments, the AR overlay is superimposed on a view of an operating field as viewed by a surgeon, updated in real time.

In another aspect, the invention is directed to a system for the rendering and real-time display of an augmented reality overlay representation of one or more dual-modality probe species (e.g., multifunctional nanoparticles) in tissue for enhanced real-time visualization of one or more tissue structures of a subject (e.g., for intraoperative, perioperative, and/or preoperative imaging), the system comprising: a dynamic motion tracker for detecting tracking sensors and for producing real-time sensor position information; and a processor and a memory having instructions stored thereon, wherein the instructions, when executed by the processor, cause the processor to: receive and/or store one or more radiological images representing emission of one or more radiolabel species of the one or more dual-modality probe species having been administered to the subject (e.g., PET, SPECT, PET/CT, SPECT/CT, etc.); and produce the real-time augmented reality (AR) overlay (e.g., 3D representation) using the one or more radiological images and the real-time sensor position information (e.g., by performing an ANN/CNN reconstruction).

In certain embodiments, the sensors are placed on/in/around the subject and/or the sensors are placed on a hands-free wearable device.

In certain embodiments, the one or more radiological images comprises one or more "still" 3D images or a time-series of 3D images, e.g., a sequence of 3D images obtained over a period of time.

In certain embodiments, the system further comprises an electronic display for display of the AR overlay superimposed on a view of the subject. In certain embodiments, the electronic display is a hands-free wearable device. In certain embodiments, the AR overlay is superimposed on a view of an operating field as viewed by a surgeon, updated in real time.

In another aspect, the invention is directed to a kit comprising any one of the systems described herein and the one or more dual-modality probe species.

In another aspect, the invention is directed to a system for the rendering and real-time display of an augmented reality overlay representation of 3D functional information derived from intrinsic tissue signals for enhanced real-time visualization of one or more tissue structures of a subject (e.g., for intraoperative, perioperative, and/or preoperative imaging), the system comprising: a dynamic motion tracker for detecting tracking sensors and for producing real-time sensor position information; a real-time NIR imaging apparatus (e.g., hyperspectral data acquisition device) for detecting near-infrared light (i) at each of a plurality of discrete wavelengths and/or (ii) over each of a plurality of discrete wavelength bands and a processor and a memory having instructions stored thereon, wherein the instructions, when executed by the processor, cause the processor to: derive real-time 3D functional information [e.g., oxygenation states, e.g., perfusion (e.g., flow) status, e.g., determined voxel-by-voxel, or segmented-volume-by-segmented-volume] using the detected NIR light at the plurality of wavelengths and/or wavelength bands (e.g., via machine learning based hyperspectral analysis or other algorithms); and produce a real-time augmented reality (AR) overlay (e.g., 3D representation) using the real-time sensor position information and the real-time 3D functional information (e.g., by performing an ANN/CNN reconstruction).

In certain embodiments, the sensors are placed on/in/around the subject and/or the sensors are placed on a hands-free wearable device.

In certain embodiments, each of the plurality of discrete wavelengths and/or wavelength bands are within a range from 400 nm to 2500 nm, e.g., each of the one or more discrete wavelengths and/or bands within NIR I (400-900 nm) and/or one or more discrete wavelengths and/or bands within NIR II (900-1700).

In certain embodiments, the instructions, when executed by the processor, cause the processor to: receive and/or store one or more previously-acquired 3D images of the subject (e.g., CT, PET, SPECT, PET/CT, SPECT/CT, etc.); and produce the real-time AR overlay using the previously-acquired 3D images of the subject, the real-time sensor position information, and the real-time 3D functional information (e.g., by performing an ANN/CNN reconstruction). In certain embodiments, the one or more previously-acquired 3D images comprises one or more "still" 3D images or a time-series of 3D images, e.g., a sequence of 3D images obtained over a period of time.

In another aspect, the invention is directed to a method for the rendering and real-time display of an augmented reality overlay representation of one or more dual-modality probe species (e.g., a multifunctional nanoparticle species or other probe comprising one or more radiolabels and one or more fluorophores) in tissue for enhanced real-time visualization of one or more tissue structures of a subject (e.g., for intraoperative, perioperative, and/or preoperative imaging), the method comprising: detecting near-infrared light, by a real-time NIR imaging apparatus (e.g., camera), at each of one or more discrete wavelengths each corresponding to an emission frequency of each of the one or more dual-modality probe species [e.g., one or more discrete wavelengths within a range from 400 nm to 2500 nm, e.g., one or more discrete wavelengths within NIR I (400-900 nm) and/or one or more discrete wavelengths within NIR II (900-1700)], said one or more probe species having been administered to the subject for accumulation in and/or about the one or more tissue structures for which visualization is to be enhanced (e.g., lymph node, nerve tissue, tumor tissue, etc.); receiving and/or storing, by a processor of a computing device, one or more radiological images (e.g., one or more "still" 3D images or a time-series of 3D images, e.g., a sequence of 3D images obtained over a period of time) representing emission of one or more radiolabel species of the administered one or more dual-modality probe species (e.g., PET, SPECT, PET/CT, SPECT/CT, etc.); receiving and/or storing, by the processor, one or more series of NIR images (e.g., one or more video streams) obtained by the real-time NIR imaging apparatus, each series corresponding to an emission frequency of one of the one or more dual-modality probe species; and producing, by the processor, a real-time augmented reality (AR) overlay (e.g., 3D representation) using the one or more radiological images and the one or more series of NIR images (e.g., by performing an ANN/CNN reconstruction).

In certain embodiments, the method further comprises detecting, by a dynamic motion tracker, one or more tracking sensors (e.g., sensors placed on/in/around the subject and/or sensors placed on a hands-free wearable device); producing, by the processor, real-time sensor position information; producing, by the processor, the real-time AR overlay using the one or more radiological images, the one or more series of NIR images, and the real-time sensor position information; rendering, by the processor, the AR overlay for display (e.g., to a surgeon, e.g., via a hands-free wearable device with tracking sensors); and updating, by the processor, the real-time AR overlay in real-time (e.g., during a surgical procedure, e.g., for assisting radiotherapy (e.g., for locating where radiotherapy should be applied), e.g., according to movement of the subject, movement of the hands-free wearable device, and/or real-time evolution of the NIR images detected by the NIR imaging apparatus).

In certain embodiments, the method further comprises displaying, via an electronic display (e.g., the hands-free wearable device), the AR overlay superimposed on a view of the subject (e.g., superimposed on a view of an operating field as viewed by a surgeon, updated in real time).

In another aspect, the invention is directed to a method for the rendering and real-time display of an augmented reality (AR) overlay representation of one or more dual-modality probe species (e.g., multifunctional nanoparticles) in tissue for enhanced real-time visualization of one or more tissue structures of a subject (e.g., for intraoperative, perioperative, and/or preoperative imaging), the method comprising: detecting tracking sensors (e.g., sensors placed on/in/around the subject and/or sensors placed on a hands-free wearable device) and producing real-time sensor position information, via a dynamic motion tracker; receiving and storing, by a processor of a computing device, one or more radiological images (e.g., one or more "still" 3D images or a time-series of 3D images, e.g., a sequence of 3D images obtained over a period of time) representing emission of one or more radiolabel species of the one or more dual-modality probe species having been administered to the subject (e.g., PET, SPECT, PET/CT, SPECT/CT, etc.); and producing, by the processor, the real-time augmented reality (AR) overlay (e.g., 3D representation) using the one or more radiological images and the real-time sensor position information (e.g., by performing an ANN/CNN reconstruction).

In certain embodiments, the method further comprises displaying, via an electronic display (e.g., the hands-free wearable device), the AR overlay superimposed on a view of the subject (e.g., superimposed on a view of an operating field as viewed by a surgeon, updated in real time).

In another aspect, the invention is directed to a method for the rendering and real-time display of a real-time augmented reality overlay representation of 3D functional information derived from intrinsic tissue signals for enhanced real-time visualization of one or more tissue structures of a subject (e.g., for intraoperative, perioperative, and/or preoperative imaging), the method comprising: detecting tracking sensors (e.g., sensors placed on/in/around the subject and/or sensors placed on a hands-free wearable device) and producing real-time sensor position information via a dynamic motion tracker; detecting, near-infrared light (i) at each of a plurality of discrete wavelengths and/or (ii) over each of a plurality of discrete wavelength bands, [e.g., a plurality of discrete wavelengths and/or wavelength bands within a range from 400 nm to 2500 nm, e.g., one or more discrete wavelengths and/or bands within NIR I (400-900 nm) and/or one or more discrete wavelengths and/or bands within NIR II (900-1700)] via a real-time NIR imaging apparatus (e.g., hyperspectral data acquisition device); computing, by a processor of a computing device, real-time 3D functional information [e.g., oxygenation states, e.g., perfusion (e.g., flow) status, e.g., determined voxel-by-voxel, or segmented-volume-by-segmented-volume] using the detected NIR light at the plurality of wavelengths and/or wavelength bands (e.g., via machine learning based hyperspectral analysis or other algorithms); and producing, by the processor, the real-time augmented reality (AR) overlay (e.g., 3D representation) using the real-time sensor position information and the real-time 3D functional information (e.g., by performing an ANN/CNN reconstruction).

In certain embodiments, the method comprises receiving and/or storing, by the processor, one or more previously-acquired 3D images of the subject (e.g., one or more "still" 3D images or a time-series of 3D images, e.g., a sequence of 3D images obtained over a period of time) (e.g., CT, PET, SPECT, PET/CT, SPECT/CT, etc.); and rendering, by the processor, the real-time AR overlay using the previously-acquired 3D images of the subject, the real-time sensor position information, and the real-time 3D functional information (e.g., by performing an ANN/CNN reconstruction).

In another aspect, the invention is directed to a system for the rendering and real-time display of an augmented reality overlay representation of one or more probe species in tissue for enhanced real-time visualization of one or more tissue structures of a subject (e.g., for intraoperative, perioperative, and/or preoperative imaging), the system comprising: a dynamic motion tracker for detecting tracking sensors and for producing real-time sensor position information; a real-time NIR imaging apparatus (e.g., hyperspectral data acquisition device) for detecting near-infrared light (i) at each of one or more discrete wavelengths and/or (ii) over each of one or more discrete wavelength bands, [e.g., a plurality of discrete wavelengths and/or wavelength bands within a range from 400 nm to 2500 nm, e.g., one or more discrete wavelengths and/or bands within NIR I (400-900 nm) and/or one or more discrete wavelengths and/or bands within NIR II (900-1700)]; and a processor and a memory having instructions stored thereon, wherein the instructions, when executed by the processor, cause the processor to: receive and/or store one or more structural images of the subject [e.g., one or more 3D images (e.g., CT, PET, SPECT, PET/CT, SPECT/CT), e.g., obtained prior to a surgical procedure or radiotherapy, e.g., one or more radiological images, e.g., representing emission of one or more radiolabel species of one or more probe species having been administered to the subject (e.g., PET, SPECT, PET/CT, SPECT/CT, etc.)]; and produce the real-time augmented reality (AR) overlay (e.g., 3D representation) using the one or more structural images of the subject, the near-infrared light detected by the real-time NIR imaging apparatus, and the real-time sensor position information (e.g., by performing an ANN/CNN reconstruction).

In certain embodiments, the one or more probe species comprise nanoparticles, e.g., multifunctional nanoparticles.

In certain embodiments, the instructions, when executed by the processor, cause the processor to produce the real-time AR overlay using the one or more radiological images, the one or more series of NIR images, and the real-time sensor position information, and wherein the instructions, when executed by the processor, cause the processor to render the AR overlay for display (e.g., to a surgeon, e.g., via a hands-free wearable device with tracking sensors), and to update the real-time AR overlay in real-time (e.g., during a surgical procedure, e.g., for assisting radiotherapy (e.g., for locating where radiotherapy should be applied), e.g., according to movement of the subject, movement of the hands-free wearable device, and/or real-time evolution of the NIR images detected by the NIR imaging apparatus).

In certain embodiments, the tracking sensors are placed on/in/around the subject and/or the sensors are placed on a hands-free wearable device.

In certain embodiments, the system further comprises an electronic display (e.g., the hands-free wearable device) for display of the AR overlay superimposed on a view of the subject. In certain embodiments, the AR overlay is superimposed on a view of an operating field as viewed by a surgeon, updated in real time.

In another aspect, the invention is directed to a kit comprising any of the systems described herein and the one or more probe species.

In another aspect, the invention is directed to a method for the rendering and real-time display of an augmented reality overlay representation of one or more probe species (e.g., nanoparticles, e.g., multifunctional nanoparticle species or other probes comprising one or more radiolabels and one or more fluorophores) in tissue for enhanced real-time visualization of one or more tissue structures of a subject (e.g., for intraoperative, perioperative, and/or preoperative imaging), the method comprising: detecting near-infrared light, by a real-time NIR imaging apparatus (e.g., camera), at each of one or more discrete wavelengths each corresponding to an emission frequency of each of the one or more probe species [e.g., one or more discrete wavelengths within a range from 400 nm to 2500 nm, e.g., one or more discrete wavelengths within NIR I (400-900 nm) and/or one or more discrete wavelengths within NIR II (900-1700)], said one or more probe species having been administered to the subject for accumulation in and/or about the one or more tissue structures for which visualization is to be enhanced (e.g., lymph node, nerve tissue, tumor tissue, etc.); receiving and/or storing, by a processor of a computing device, one or more radiological images (e.g., one or more "still" 3D images or a time-series of 3D images, e.g., a sequence of 3D images obtained over a period of time) representing emission of one or more radiolabel species of the administered one or more probe species (e.g., PET, SPECT, PET/CT, SPECT/CT, etc.); receiving and/or storing, by the processor, one or more series of NIR images (e.g., one or more video streams) obtained by the real-time NIR imaging apparatus, each series corresponding to an emission frequency of one of the one or more probe species; and producing, by the processor, a real-time augmented reality (AR) overlay (e.g., 3D representation) using the one or more radiological images and the one or more series of NIR images (e.g., by performing an ANN/CNN reconstruction).

In certain embodiments, the method further comprises detecting, by a dynamic motion tracker, one or more tracking sensors (e.g., sensors placed on/in/around the subject and/or sensors placed on a hands-free wearable device); producing, by the processor, real-time sensor position information; producing, by the processor, the real-time AR overlay using the one or more radiological images, the one or more series of NIR images, and the real-time sensor position information; rendering, by the processor, the AR overlay for display (e.g., to a surgeon, e.g., via a hands-free wearable device with tracking sensors); and updating, by the processor, the real-time AR overlay in real-time (e.g., during a surgical procedure, e.g., for assisting radiotherapy (e.g., for locating where radiotherapy should be applied), e.g., according to movement of the subject, movement of the hands-free wearable device, and/or real-time evolution of the NIR images detected by the NIR imaging apparatus).

In certain embodiments, the method further comprises displaying, via an electronic display (e.g., the hands-free wearable device), the AR overlay superimposed on a view of the subject (e.g., superimposed on a view of an operating field as viewed by a surgeon, updated in real time).

In certain embodiments, the method further comprises administering treatment (e.g., radiation therapy) to the subject (e.g., in a clinical setting, e.g., in a post-operative setting), wherein the treatment is informed by and/or guided by the display of the augmented reality overlay representation.

Elements of embodiments involving one aspect of the invention (e.g., methods) can be applied in embodiments involving other aspects of the invention (e.g., systems), and vice versa.

BRIEF DESCRIPTION OF THE FIGURES

Drawings are presented herein for illustration purposes, not for limitation. The foregoing and other objects, aspects, features, and advantages of the present disclosure will become more apparent and better understood by referring to the following description taken in conjunction with the accompanying drawings, in which.

Figure 1:
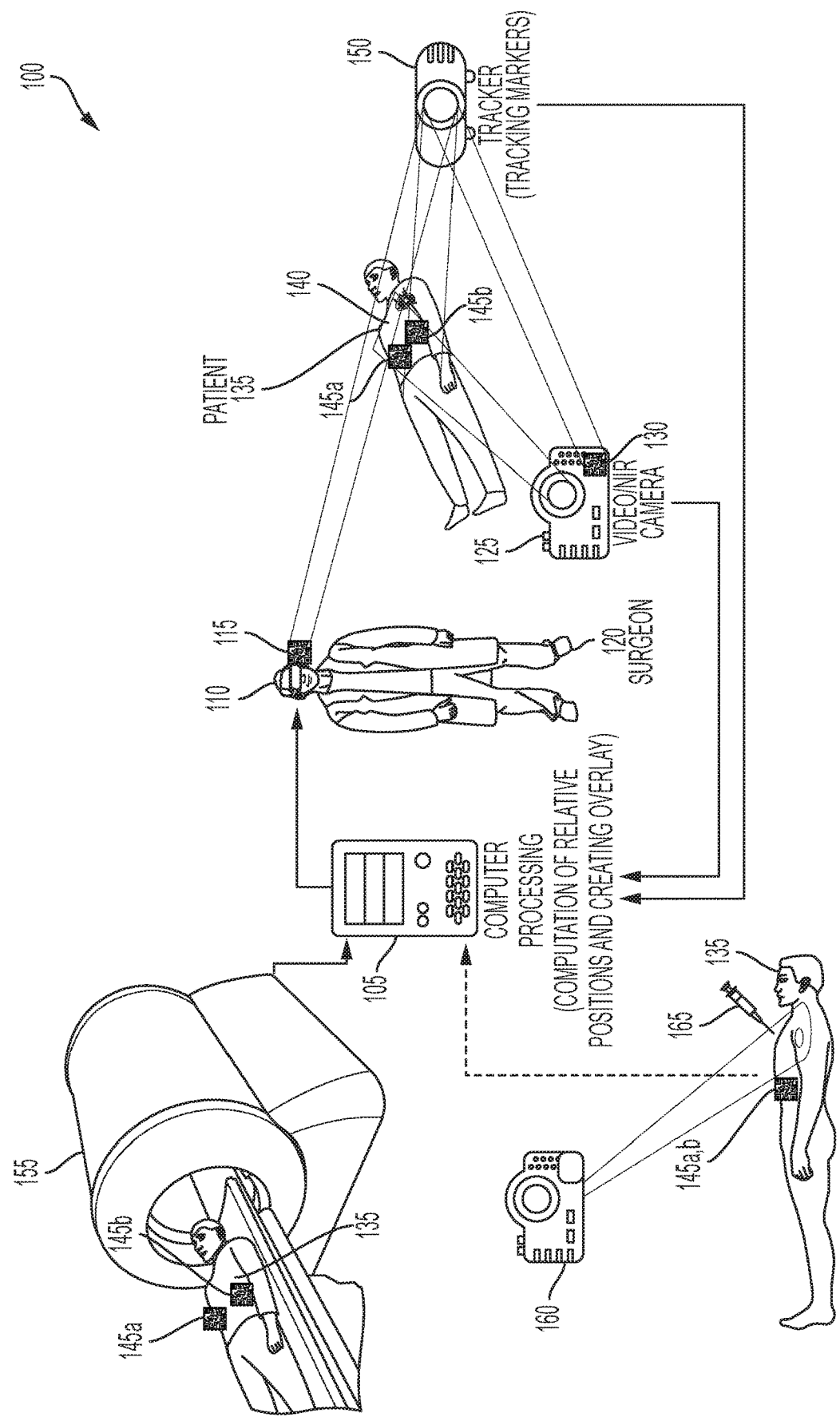
FIG. 1 is a schematic diagram of a system for the rendering and real-time display of an augmented reality overlay representation of one or more probe species in tissue for enhanced real-time visualization of one or more tissue structures of a subject, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

Elements of embodiments described with respect to a given aspect of the invention may be used in various embodiments of another aspect of the invention. For example, it is contemplated that features of dependent claims depending from one independent claim can be used in apparatus, articles, systems, and/or methods of any of the other independent claims.

Headers are provided for the convenience of the reader—the presence and/or placement of a header is not intended to limit the scope of the subject matter described herein.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

FIG. 1 shows a schematic diagram of a system 100 for the rendering and real-time display of an augmented reality (AR) overlay representation of probe species in tissue for enhanced real-time visualization of tissue structure(s) of a subject (e.g., a patient) 135, according to an illustrative embodiment. System 100 comprises a real-time imaging apparatus (e.g., video/NIR camera) 125 for detecting, in real time, near-infrared light at each of one or more discrete wavelengths. Each detected wavelength corresponds to an emission frequency of each of the one or more dual-modality probe species. The wavelengths may include one or more discrete wavelengths within a range from 400 nm to 2500 nm, one or more discrete wavelengths within the NIR I window (400-900 nm), and/or one or more discrete wavelengths within the NIR II window (900-1700). The one or more dual-modality probe species have been administered to subject 135 and have accumulated in and/or about the one or more tissue structures (e.g., lymph node, nerve tissue, tumor tissue, or the like) for which visualization is to be enhanced. For example, as shown in the illustrative example of FIG. 1, dual-modality probe species have accumulated in certain lymph nodes 140 of patient 135.

In certain embodiments, the dual-modality probe species is a multifunctional nanoparticle species. For example, the probe species may include one or more of the probe species described in U.S. Pat. No. 9,625,456, issued Apr. 18, 2017, U.S. Patent Application No. 62/510,859, filed May 25, 2017, International Patent Application No. PCT/US16/30752, filed May 4, 2016, International Patent Application No. PCT/US17/63641, filed Nov. 29, 2017, International Patent Application No. PCT/US17/30056, filed Apr. 28, 2017, International Patent Application No. PCT/US17/39620, filed Jun. 28, 2017, U.S. Provisional Patent Application No. 62/590,507 filed Nov. 24, 2017, International Patent Application No. PCT/US15/65816 filed Dec. 15, 2015, and International Patent Application No. PCT/US16/66969 filed Dec. 15, 2016, the contents of each of which are hereby incorporated in their entirety by reference. In some embodiments, the dual-modality probe species is another probe comprising one or more radiolabels and one or more fluorophores.

System 100 also includes a processor and memory, for example, of computer 105. The processor receives and/or stores one or more series of NIR images (e.g., one or more video streams) obtained by the real-time NIR imaging apparatus 125. Illustrative examples of computer hardware and network implementations related to the processor and memory are described with reference to FIG. 4 and FIG. 5 below. Each series of NIR images received and/or stored by the processor corresponds to an emission frequency of one of the administered dual-modality probe species. The processor also receives and/or stores one or more radiological images representing emission of one or more radiolabel species (e.g., an isotopic label, e.g., $^{89}$Zr) of the administered one or more dual-modality probe species. For example, the radiological images may include one or more "still" 3D images or a time-series of 3D images (e.g., a sequence of 3D images obtained over a period of time) obtained using a radiological imaging apparatus (e.g., a PET, SPECT, PET/CT, or SPECT/CT imaging system) 155.

The processor (e.g., of computer 105) produces a real-time augmented reality (AR) overlay (e.g., 3D representation) using the one or more radiological images and the one or more series of NIR images. For example, the AR overlay may be produced by performing an artificial neural network (ANN)/convolutional neural network (CNN) reconstruction. In certain embodiments, system 100 includes a hands-free wearable device 110 for display of the AR overlay superimposed on a view of the subject (e.g., superimposed on a view of an operating field as viewed by surgeon 120 and updated in real time).

In certain embodiments, the system includes a dynamic motion tracker 150 for detecting tracking sensors and producing real-time sensor position information. Tracking sensors act as fiducial markers (e.g., fiducials) for determining the relative positions of the imaging apparatus 125 (e.g., via tracking sensor(s) 130), the imaged tissue structure(s) 140 (e.g., via tracking sensors 145a,b), and/or the hands-free wearable device 110 (e.g., via tracking sensor(s) 115). The real-time sensor position information produced by the dynamic motion tracker 150 using the tracking sensors is used, by the processor, along with the one or more radiological images and the one or more series of NIR images to produce the real-time AR overlay. The processor may then render the AR overlay for display (e.g., for viewing by surgeon 120) via a hands-free wearable device 110 with tracking sensors 115 and updates the real-time AR overlay in real-time. For example, the rendered AR overlay can be updated during a surgical procedure according to movement of the subject 135, movement of the hands-free wearable device 110, and/or real-time evolution of the NIR images detected by the NIR imaging apparatus 125.

Still referring to FIG. 1, in certain embodiments, the processor produces a real-time AR overlay using radiological images along with the position information obtained via the dynamic motion tracker 150 and the corresponding tracker sensors (e.g., tracker sensors 145a,b located on the body of patient 135 and tracker sensor(s) 115 located on the hands-free wearable device 100). In other words, in some embodiments, the processor does not use a series of NIR images to produce the real-time AR overlay. Instead, for example, fluorescent light emitted by the administered multimodal probe may simply be viewed via the naked eye by surgeon 120 such that enhancement of the fluorescent signal (e.g., by producing and rendering a real-time VR overlay that is based in part on the series of NIR images) may not be required.

In this embodiment, the processor (e.g., of computer 105) receives and/or stores one or more radiological images (e.g., one or more "still" 3D images or a time-series of 3D images, e.g., a sequence of 3D images obtained over a period of time) representing emission of one or more radiolabel species of the one or more dual-modality probe species having been administered to the subject 135 (e.g., PET, SPECT, PET/CT, SPECT/CT, or the like). The processor produces a real-time augmented reality (AR) overlay (e.g., 3D representation) using the one or more radiological images and the real-time sensor position information from the dynamic motion tracker (e.g., by performing an ANN/CNN reconstruction).

In certain embodiments, the present disclosure is directed to a kit comprising any of the systems described herein and one or more dual-modality probe species.

Probe Species (e.g., Dual-Modality Probe Species)

In certain embodiments, the probe species comprises a nanoparticle. In certain embodiments, the nanoparticle comprises silica, polymer (e.g., poly(lactic-co-glycolic acid) (PLGA)), biologics (e.g., protein carriers), and/or metal (e.g., gold, iron). In certain embodiments, the nanoparticle is a "C dot" as described in U.S. Publication No. 2013/0039848 A1 by Bradbury et al., which is hereby incorporated by reference in its entirety.

In certain embodiments, the nanoparticle is spherical. In certain embodiments, the nanoparticle is non-spherical. In certain embodiments, the nanoparticle is or comprises a material selected from the group consisting of metal/semimetal/non-metals, metal/semi-metal/non-metal-oxides, -sulfides, -carbides, -nitrides, liposomes, semiconductors, and/or combinations thereof. In certain embodiments, the metal is selected from the group consisting of gold, silver, copper, and/or combinations thereof.

In certain embodiments, the nanoparticle is a nanoparticle as described in U.S. Pat. No. 8,409,876 entitled "Fluorescent Silica-Based Nanoparticles" filed on Oct. 14, 2009, U.S. Pat. No. 8,298,677 entitled "Fluorescent Silica-Based Nanoparticles" filed on May 2, 2006, U.S. Pat. No. 8,084,001 entitled "Photoluminescent Silica-Based Sensors and Methods of Use" filed on May 2, 2006, U.S. Pat. No. 8,961,825 entitled "Fluorescent Silica Nanoparticles Through Silica Densification" filed on Apr. 27, 2012, U.S. Patent Publication No. US 2015-0366995 A1 entitled "Mesoporous Oxide Nanoparticles and Methods of Making and Using Same" filed on Dec. 22, 2014, U.S. Patent Publication No. US 2016-0018404 A1 entitled "Multilayer Fluorescent Nanoparticles and Methods of Making and Using Same" filed on Aug. 19, 2015, U.S. Patent Publication No. US 2018-0133346 A1 entitled "Ultrasmall Nanoparticles and Methods of Making and Using Same" filed on Nov. 2, 2017, International Patent Application No. PCT/US18/33755 entitled "Functionalized Nanoparticles and Methods of Making Same" filed on May 21, 2018, U.S. Pat. No. 9,625,456, "Fluorescent Silica-Based Nanoparticles," and International Patent Application No. PCT/US18/33098 entitled "Ultrasmall Nanoparticles Labeled with Zirconium-89 and Methods Thereof" filed on May 17, 2018, the contents of each of which are hereby incorporated by reference in their entireties.

In certain embodiments, the nanoparticle is selected from the photoswitchable nanoparticles described by Kohle et al., "Sulfur- or Heavy Atom-Containing Nanoparticles, Methods or Making the Same, and Uses Thereof," in International Application No. PCT/US18/26980 filed on Apr. 10, 2018, the photoluminescent silica-based sensors described by Burns et al. "Photoluminescent Silica-Based Sensors and Methods of Use" in U.S. Pat. No. 8,084,001 B1, and/or the nanoparticles described by Bradbury et al., "Ultrasmall Nanoparticles Labeled with Zirconium-89 and Methods Thereof," International Patent Application No. PCT/US18/33098, filed on May 17, 2018. In certain embodiments, the nanoparticle is a modification or combination of any of such compositions.

In certain embodiments, the probe species comprises a nanoparticle composition described by International Patent Application No. PCT/US19/29598 entitled "Nanotherapeutic systems and methods using particle-driven photodynamic therapy (PDT)," filed on Apr. 29, 2019, the disclosure of which is hereby incorporated by reference in its entirety. In certain embodiments, the probe species comprises a nanoparticle composition that comprises a PDT-active moiety (e.g., Cy5, e.g., methylene blue, e.g., Cy5.5) associated (e.g., covalently bound, e.g., non-covalently bound) with silica-based nanoparticles.

In certain embodiments, the fluorophore moiety is Cy5, i.e. Cyanine 5:

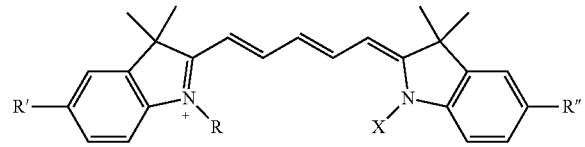

wherein R is —CH$_3$, R' is —H, R" is —H, and X is —(CH$_2$)$_5$—C(O)—, or any suitable salt thereof. In certain embodiments, either or both of R' and R" is —S(O)$_2$—OH or a suitable sulfonate (i.e. —S(O)$_2$—O$^-$) salt thereof. Cy5 can be associated with the described nanoparticle compositions using any suitable means, e.g., conjugation via an activated form of the acid (X is —(CH$_2$)$_5$—C(O)—OH) such as the NHS ester, which can be purchased or can be made using N-hydroxysuccinimide. Other forms of Cy5 can be used in accordance with the systems and methods described by the present disclosure, e.g., equivalents and/or analogues thereof (e.g., any of the foregoing wherein R is —CH$_2$CH$_3$), associated with the described nanoparticle compositions.

In certain embodiments, the fluorophore moiety is Cy5.5, i.e. Cyanine 5.5:

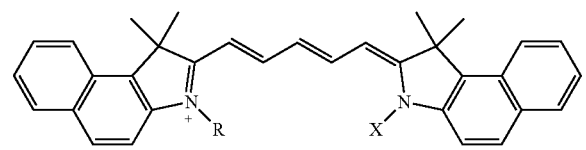

wherein R is —CH$_3$ and X is —(CH$_2$)$_5$—C(O)—, or any suitable salt thereof. Cy5.5 can be associated with the described nanoparticle compositions using any suitable means, e.g., conjugation via an activated form of the acid (X is —(CH$_2$)$_5$—C(O)—OH) such as the NHS ester, which can be purchased or can be made using N-hydroxysuccinimide. Other forms of Cy5.5 can be used in accordance with the systems and methods described by the present disclosure, e.g., equivalents and/or analogues thereof (e.g., R is —CH$_2$CH$_3$), associated with the described nanoparticle compositions.

In certain embodiments, the fluorophore is methylene blue or 3,7-Bis(dimethylamino)phenothiazin-5-ium chloride. In certain embodiments, the fluorophore comprises:

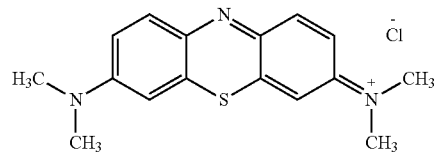

Methylene blue (MB) can be associated with the described nanoparticle compositions using any suitable means, e.g., conjugation via an activated form of the acid (X is —(CH$_2$)$_5$—C(O)—OH) such as the NHS ester, which can be purchased or can be made using N-hydroxysuccinimide. Other forms of methylene blue can be used in accordance with the systems and methods described by the present disclosure, e.g., equivalents and/or analogues thereof, associated with the described nanoparticle compositions.

A probe species can comprise various amounts of PDT-active moieties. Without wishing to be bound to any theory, it is considered that the number of PDT-active moieties associated to the nanoparticle correlates to the amount of PDT-active moieties precursor used in the synthesis of the probe species. For example, for nanoparticles having a diameter below 10 nm, such nanoparticles may have on average from about 1 to about 20 (e.g., from about 1 to about 10, e.g., from about 1 to about 5, e.g., from about 1 to about 2) PDT-active moieties per probe species.

In certain embodiments, the probe species can be excellent generators of singlet oxygen, which is associated with high cancer cell kill efficiency. Furthermore, attaching a PDT-active moiety to an ultrasmall nanoparticle offers advantages (e.g., average overall particle diameter, with attached PDT-active moiety, no greater than 20 nm, e.g., no greater than 15 nm, e.g., no great than 10 nm), such advantages including the ability to track/visualize the nanoparticle composition (while retaining renal clearance of the nanoparticle), improved localization of the nanoparticle composition, e.g., at locations requiring treatment, the ability to achieve higher local concentrations or reactive oxygen species (ROS) generation at areas requiring treatment, the ability to circumvent immune evasion/immunomodulatory mechanisms employed by tumors, the ability to increase tumor immunogenicity to elicit a multi-antigen vaccination effect without the need for a priori knowledge of tumor antigens, and the ability to modulate tumor microenvironment.

In certain embodiments, the nanoparticle may comprise metal/semi-metal/non-metal oxides including silica (SiO$_2$), titania (TiO$_2$), alumina (Al$_2$O$_3$), zirconia (Z$_r$O2), germania (GeO$_2$), tantalum pentoxide (Ta$_2$O$_5$), NbO$_2$, and/or non-oxides including metal/semi-metal/non-metal borides, carbides, sulfide and nitrides, such as titanium and its combinations (Ti, TiB$_2$, TiC, TiN).

The probe species may comprise one or more polymers, e.g., one or more polymers that have been approved for use in humans by the U.S. Food and Drug Administration (FDA) under 21 C.F.R. § 177.2600, including, but not limited to, polyesters (e.g., polylactic acid, poly(lactic-co-glycolic acid), polycaprolactone, polyvalerolactone, poly(1,3-dioxan-2-one)); polyanhydrides (e.g., poly(sebacic anhydride)); polyethers (e.g., polyethylene glycol); polyurethanes; polymethacrylates; polyacrylates; polycyanoacrylates; copolymers of PEG and poly(ethylene oxide) (PEO).

The probe species may comprise one or more degradable polymers, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly (glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly (beta-amino esters), which may be suitable for use in accordance with the present application.

In certain embodiments, the probe species can have or be modified to have one or more functional groups. Such functional groups (within or on the surface of a nanoparticle) can be used for association with any agents (e.g., detectable entities, targeting entities, therapeutic entities, or PEG). In addition to changing the surface charge by introducing or modifying surface functionality, the introduction of different functional groups allows the conjugation of linkers (e.g., (cleavable or (bio-)degradable) polymers such as, but not limited to, polyethylene glycol, polypropylene glycol, PLGA), targeting/homing agents, and/or combinations thereof.

In certain embodiments, the probe species comprises a nanoparticle that comprises one or more targeting ligands attached to the nanoparticle as described in International Patent Application No. PCT/US17/63641, "Inhibitor-Functionalized Ultrasmall Nanoparticles and Methods Thereof," filed Nov. 29, 2017, published as WO/2018/102372, which is incorporated herein by reference in its entirety. In certain embodiments, the nanoparticle comprises (e.g., has attached) one or more targeting ligands, e.g., for targeting cancer tissue/cells of interest. In certain embodiments, the nanoparticle comprises one or more targeting ligands (or moieties) (e.g., attached thereto), such as, but not limited to, small molecules (e.g., folates, dyes, etc), aptamers (e.g., A10, AS1411), polysaccharides, small biomolecules (e.g., folic acid, galactose, bisphosphonate, biotin), oligonucleotides, and/or proteins (e.g., (poly)peptides (e.g., αMSH, RGD, octreotide, AP peptide, epidermal growth factor, chlorotoxin, transferrin, etc), antibodies, antibody fragments, proteins). In certain embodiments, the nanoparticle comprises one or more contrast/imaging agents (e.g., fluorescent dyes, (chelated) radioisotopes (SPECT, PET), MR-active agents, CT-agents), and/or therapeutic agents (e.g., small molecule drugs, therapeutic (poly)peptides, therapeutic antibodies, radioisotopes, chelated radioisotopes). In certain embodiments, the radioisotope used as a contrast/imaging agent and/or therapeutic agent comprises any one or more of $^{99m}$Tc, $^{111}$In, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{11}$C, $^{13}$N, $^{15}$O, $^{18}$F, $^{186}$Re, $^{188}$Re, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, $^{89}$Zr, $^{225}$Ac, and $^{192}$Ir.

In certain embodiments, PET (Positron Emission Tomography) tracers are used as imaging agents. In certain embodiments, PET tracers comprise $^{89}$Zr, $^{64}$Cu, $^{225}$Ac, and/or $^{18}$F. In certain embodiments, the PET tracer comprises fluorodeoxyglucose. In certain embodiments, the nanoparticle includes these and/or other radiolabels. In certain embodiments, the one or more targeting ligands (or moieties) can be of the same type, or can be different species.

In certain embodiments, the probe species comprises one or more fluorophores. Fluorophores comprise fluorochromes, fluorochrome quencher molecules, any organic or inorganic dyes, metal chelates, or any fluorescent enzyme substrates, including protease activatable enzyme substrates. In certain embodiments, fluorophores comprise long chain carbophilic cyanines. In other embodiments, fluorophores comprise DiI, DiR, DiD, and the like. Fluorochromes comprise far red, and near infrared fluorochromes (NIRF). Fluorochromes include but are not limited to a carbocyanine and indocyanine fluorochromes. In certain embodiments, imaging agents comprise commercially available fluorochromes including, but not limited to Cy5.5, Cy5 and Cy7 (GE Healthcare); AlexaFlour660, AlexaFlour680, AlexaFluor750, and AlexaFluor790 (Invitrogen); VivoTag680, VivoTag-5680, and VivoTag-S750 (VisEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source) and Kodak X-SIGHT 650, Kodak X-SIGHT 691, Kodak X-SIGHT 751 (Carestream Health).

Targeted Probe Species (e.g., Dual-Modality), and Applications

In certain embodiments, the present disclosure describes targeted probe species (e.g., dual-modality) and related applications. In certain embodiments, the targeted probe specie is a probe species as described in International (PCT) Patent Application No. PCT/US17/63641, "Inhibitor-Functionalized Ultrasmall Nanoparticles and Methods Thereof," the disclosure of which is hereby incorporated by reference in its entirety.

For example, the targeted probe species comprises prostate cancer (PC)-targeting nanoparticles (e.g., PC-targeting dots (C' dots)). PC-targeting nanoparticles can be used to detect disease and enable more reliable staging of disease. This technology provides the ability to identify patients potentially curable by surgical resection versus those for whom systemic therapy would be required.

Targeted probe species such as PC-targeting nanoparticles offer at least the following advantages compared to alternative technologies: (1) an "all-in-one" dual-modality and clinically-translatable inhibitor (e.g., PSMA inhibitor, e.g., GRPr inhibitor)-targeting platform for perioperative management of PC; (2) utilization of spectrally-distinct PC-targeting C' dots and fluorescence-based multiplexing strategies for real-time evaluation of multiple molecular cancer phenotypes; (3) qualification of reliable staging biomarkers targeting different biological processes for direct clinical validation; (4) characterization of inhibitor expression levels for new metastatic PC subclones and human prostate organoid-based models that may more faithfully reproduce human disease; (5) efficient optimization of new surface designs for renally-clearable PC-targeted C' dots which overcome high non-specific uptake in radiosensitive organs (e.g., kidney, salivary glands), where such non-specific uptake has limited radiotherapeutic dosing and treatment efficacy; (6) use of particle-encapsulated NIR dyes to obviate attendant losses in bioactivity seen with NIR dye-conjugated inhibitor, the latter precluding NIR-driven optical applications; and (7) chemical adaptation of linker-peptide chemistries prior to C' dot attachment to preserve pharmacophore activity while enhancing radiolabeling and tumor-targeting efficiencies.

In certain embodiments, the targeted probe species is a probe species as described in International (PCT) Patent Application No. PCT/US17/30056, "Compositions and Methods for Targeted Particle Penetration, Distribution, and Response in Malignant Brain Tumors," the disclosure of which is hereby incorporated by reference in its entirety. For example, a targeted probe species demonstrate enhanced penetration of tumor tissue (e.g., brain tumor tissue) and diffusion within the tumor interstitium, e.g., for treatment of cancer (e.g., primary and metastatic brain tumors) that can be used in accordance with the embodiments of the present disclosure. Such targeted probe species are capable of targeting tumor-associated macrophages, microglia, and/or other cells in a tumor microenvironment using such nanoparticle conjugates. Moreover, a targeted probe species can be used for treating targets in both the tumor and surrounding microenvironment, thereby enhancing efficacy of cancer treatment. Use of the targeted probe species described herein with other conventional therapies, including chemotherapy, radiotherapy, immunotherapy, and the like, is also envisaged.

In certain embodiments, the targeted probe species comprise one or more targeting moieties (e.g., a targeting peptide) (e.g., a tumor-targeting moiety, e.g., an RGD-containing moiety, e.g., cRGDY, to target integrins (integrin receptors) and/or a microenvironment-targeting moiety e.g., αMSH to target melanocortin-1 receptors), (e.g., for delivering the drug moiety (e.g., small molecule inhibitors, SMIs) (e.g., to integrin- and/or melanocortin-1 (MC1)-expressing cells (e.g., tumor, macrophages))). In certain embodiments, the targeted probe species comprises from 1 to 100 (e.g., from 1 to 60, e.g., from 1 to 20) discrete targeting moieties (e.g., of the same type or of different types).

In certain embodiments, the targeted probe specie is a probe species as described in International (PCT) Patent Application No. PCT/US17/39620, "Imaging Systems and Methods for Particle-Driven, Knowledge-Based, and Predictive Cancer Radiogenomics," the disclosure of which is hereby incorporated by reference in its entirety. For example, the targeted probe species can be used in particle-driven radiogenomics systems and methods, for example, to identify imaging features for prediction of intratumoral and interstitial nanoparticle distributions in the tissue of a subject (e.g., in a metastatic disease that goes to the brain, e.g., in low grade and/or high-grade brain cancers (e.g., gliomas)). In this embodiment, targeted probe species may have cancer-targeting ligands and/or therapeutics attached thereto and may be administered for in vivo imaging/tracking.

Moreover, diagnostic, therapeutic, and theranostic (diagnostic and therapeutic) platforms featuring such dual-modality and/or targeted probe species are described for treating targets in both the tumor and surrounding microenvironment, thereby enhancing efficacy of cancer treatment. Use of the dual-modality and/or targeted probe species described herein with other conventional therapies, including chemotherapy, radiotherapy, immunotherapy, and the like, is also envisaged.

Moreover, use of radiolabels and/or fluorescent markers attached to (or incorporated in or on, or otherwise associated with) the targeted probe species provide quantitative assessment of particle uptake and monitoring of treatment response. In various embodiments, modular linkers are described for incorporating targeting ligands to develop a drug delivery system with controlled pharmacological properties. The described platforms determine the influence of targeting on nanoparticle penetration and accumulation, thereby establishing an adaptable platform for improved delivery of a range of tractable SMIs, for example, to primary and metastatic brain tumors (e.g., gliomas (e.g., high grade gliomas, e.g., low grade gliomas)).

In certain embodiments, the targeted probe species comprises one or more targeting ligands (or moieties) (e.g., attached thereto), such as, but not limited to, small molecules (e.g., folates, dyes, etc), aptamers (e.g., A10, AS1411), polysaccharides, small biomolecules (e.g., folic acid, galactose, bisphosphonate, biotin), oligonucleotides, and/or proteins (e.g., (poly)peptides (e.g., αMSH, RGD, octreotide, AP peptide, epidermal growth factor, chlorotoxin, transferrin, etc), antibodies, antibody fragments, proteins, etc.). In certain embodiments, the targeted probe specie comprises one or more contrast/imaging agents (e.g., fluorescent dyes, (chelated) radioisotopes (SPECT, PET), MR-active agents, CT-agents), and/or therapeutic agents (e.g., small molecule drugs, therapeutic (poly)peptides, therapeutic antibodies, (chelated) radioisotopes, etc).

In some embodiments, a nanoparticle has a diameter of less than 300 nm, as defined by the National Science Foundation. In some embodiments, a nanoparticle has a diameter of less than 100 nm as defined by the National Institutes of Health. In some embodiments, the nanoparticle (inclusive of any ligands or other attached or associated species), is no greater than about 50 nm in diameter (e.g., no greater than 20 nm, e.g., no greater than about 15 nm, e.g., no greater than about 10 nm). In certain embodiments, the nanoparticles have an average diameter no greater than about 50 nm. In certain embodiments, the nanoparticles have an average diameter no greater than 20 nm. In certain embodiments, the nanoparticles have an average diameter from about 5 nm to about 7 nm.

In certain embodiments, each of the targeted probe species comprises (e.g., has attached) one or more targeting ligands, e.g., for targeting cancer tissue/cells of interest.

In certain embodiments, the number of ligands attached to the nanoparticle may range from about 1 to about 100, from about 1 to about 60, from about 1 to about 20, from about 2 to about 15, from about 3 to about 10, from about 1 to about 10, or from about 1 to about 6. A small number of the ligands attached to the nanoparticle helps maintain the hydrodynamic diameter of the present nanoparticle which meets the renal clearance cutoff size range. However, in certain embodiments, more than 100 ligands are used.

In certain embodiments, a therapeutic agent may be attached to the targeted probe species. The therapeutic agents include antibiotics, antimicrobials, antiproliferatives, antineoplastics, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, extracellular matrix components, vasodialators, thrombolytics, anti-metabolites, growth factor agonists, antimitotics, statin, steroids, steroidal and non-steroidal anti-inflammatory agents, angiotensin converting enzyme (ACE) inhibitors, free radical scavengers, PPAR-gamma agonists, small interfering RNA (siRNA), microRNA, and anti-cancer chemotherapeutic agents. The therapeutic agents encompassed by the present embodiment also include radionuclides, for example, $^{90}$Y, $^{131}$I and $^{177}$Lu. The therapeutic agent may be radiolabeled, such as labeled by binding to radiofluorine $^{18}$F.

Example therapeutics and/or drugs that can be used include RTK inhibitors, such as dasatinib and gefitinib, can target either platelet-derived growth factor receptor (PDGFR) or EGFRmt+ expressed by primary tumor cells of human or murine origin (e.g., genetically engineered mouse models of high-grade glioma, neurospheres from human patient brain tumor explants) and/or tumor cell lines of non-neural origin. Dasatinib and gefitinib analogs can be synthesized to enable covalent attachment to several linkers without perturbing the underlying chemical structure defining the active binding site.

In certain embodiments, the targeted probe species is a probe species as described in International (PCT) Patent Application No. PCT/US18/38973, "Systems and Methods for Super-Resolution Optical Imaging Technologies and/or Nanosensor-Driven Patient Monitoring and/or Treatment," the disclosure of which is hereby incorporated by reference in its entirety. In this embodiment, the targeted probe species comprise nanoparticles (e.g., nanosensors and photoswitchable nanoparticles) that are used to monitor and/or track changes in environmental conditions and/or analytes in the cellular microenvironment before, during, and/or after surgical procedures. For example, the nanoparticles can detect changes in reactive oxygen species (ROS), pH, pH perturbations, iron levels, calcium, glutathione, and/or amino acids such as leucine, glutamine, arginine, and others, e.g., in the cellular microenvironment. The systems and methods may provide a map of perfusion, perfusion alterations, and/or oxygen/pH status before, during, and/or after surgery. Assessment of analytes may be qualitative or quantitative.

In certain embodiments, the targeted probe species is a linear or cyclic nerve binding peptide. For example, the linear or cyclic nerve binding peptide is as described in International (PCT) Patent Application No. PCT/US15/65816, "Cyclic Peptides with Enhanced Nerve-Binding Selectivity, Nanoparticles Bound with Said Cyclic Peptides, and Use of Same for Real-Time In Vivo Nerve Tissue Imaging," the disclosure of which is hereby incorporated by reference in its entirety. In certain embodiments, the targeted probe specie targets nerves (e.g., motor nerves, e.g., sensory nerves), muscle tissue, a lymph node, or parathyroid tissue as described in International (PCT) Patent Application No. PCT/US 16/66969, "Imaging Systems and Methods for Tissue Differentiation, e.g., for Intraoperative Visualization," the disclosure of which is hereby incorporated by reference in its entirety. Such targeted probe species can be used with a multiplex platform to graphically differentiate specific nerves (e.g., sensory nerves vs. motor nerves) for nerve transplants and other surgeries and/or graphically differentiate between different types of lymph nodes and/or lymphatic pathways, e.g., to safely and effectively perform vascularized lymph node transplantation in the treatment of lymphedema.

Example NIR Imaging Apparatus:

In certain embodiments, the NIR imaging apparatus is a multichannel imaging system as described in International (PCT) Patent Application No. PCT/US14/73053, "Systems, Methods, and Apparatus for Multichannel Imaging of Fluorescent Sources in Real Time," the disclosure of which is hereby incorporated by reference in its entirety. For example, the multichannel imaging camera is capable of simultaneously imaging, in real-time, different fluorescent sources within a subject using a portable multichannel fluorescent camera. In certain embodiments, the multichannel imaging camera is a portable imaging system capable of detecting light from multiple probes species simultaneously with high signal-to-noise ratio. Such a system offers advantages over pre-existing systems that cannot simultaneously detect and distinguish more than one fluorescent probe species in real-time.

Various embodiments and configurations of the systems described herein and their components are described in Sections A-E below.

A. Pre-Operative and/or Perioperative Imaging System(s).

In some embodiments, images are obtained prior to a surgery (e.g., pre-operatively, e.g., using imaging apparatus 155 and/or 165 of FIG. 1) and are used for producing an AR overlay (e.g., for use in image reconstruction techniques and for producing 3D imaging volumes, e.g., to be registered in real-time for presentation to the surgeon). Images may also be obtained perioperatively (e.g., images may be obtained just before or near the beginning of a surgical procedure) and/or intraoperatively (e.g., images are obtained during a surgical procedure). For example, radiological or functional imaging may be performed intraoperatively following a first stage of a surgical procedure to assess and/or plan the next steps of the procedure.

As described above, in some embodiments, a radiological imaging apparatus (e.g., apparatus 155 of FIG. 1, e.g., a PET or SPECT imaging system) is used to image a radiolabeled probe. The radiolabeled probe may be, for example, a dual-modality (PET-optical) cancer-targeting nanoparticle probe. This allows structures that the probe concentrates within or otherwise associates with, to be imaged. In some embodiments, 3D anatomical imaging (e.g., CT or MRI) or other 2D or 3D anatomical imaging (e.g., ultrasound, e.g., 2D or 3D x-ray radiography) is performed. This imaging can be performed in combination with radiological imaging such as PET or SPECT imaging (e.g., PET/CT imaging, e.g., SPECT/CT imaging).

In some embodiments, NIR fluorescent images of a probe (e.g., a dual-modality probe) are, optionally, obtained pre-operatively, as shown in the illustrative example of FIG. 1. For example, NIR imaging apparatus 160 can be used to image a dual-modality probe or other fluorescent probe 165 which is administered to patient 135 before or in preparation for a medical procedure (e.g., a surgical procedure). Images of the probe may include fiducial markers associated with tracking sensors 145a,b. for orientation/registration. Alternatively (or additionally), the location of fiducial markers may be otherwise detected (e.g., via a tracker) and used for orientation/registration of the NIR fluorescent images. These pre-operative NIR image(s) can be used for producing the real-time augmented reality (AR) overlay. In some embodiments, a pre-operative NIR image of an administered probe 165 is used as a fiducial marker itself in place of or in combination with the fiducial tracking sensors. For example, probe 165 may interact with a tissue structure in a manner that does not change substantially over the time course of a medical procedure, allowing the essentially static pre-operative NIR images to act as a fiducial marker for orienting or otherwise positionally registering the AR overlay (e.g., in 2D or 3D).

B. NIR Imaging Apparatus (e.g., Video/NIR Camera)

In some embodiments, imaging apparatus 125 also captures a color (e.g., RGB) video signal (or a separate video camera can be used to capture the color video signal). In certain embodiments, imaging apparatus 125 captures, simultaneously and in real time, (i) a stream of high-resolution visible (color) images and (ii) narrowband, fine-tuned near-infrared (NIR) fluorescent images. Fluorescent images can include multiple channels (e.g., each channel being video at a particular NIR wavelength corresponding to a type of probe). The probe may be a dual-modality (PET-optical) cancer-targeting nanoparticle probe (e.g., for multiplexed imaging) such as those described above. In some embodiments, imaging apparatus 125 is simply a video camera. For example, fluorescence of the NIR probe may be seen by the unaided eye (e.g., of surgeon 120) during surgery, and enhancement of this fluorescence may not be required.

In some embodiments, one or more real-time NIR signals (e.g., within the NIR I window and/or within the NIR II window) is/are used in reconstruction of the AR overlay for (a) real-time nanoparticle probe visualization (e.g., on or beneath the surface of the skin); and/or (b) so that the nanoparticle probe can serve as an additional (or sole) "fiducial" marker detected intraoperatively for real-time registration/adjustment of the AR overlay (or otherwise used in reconstruction of the AR overlay). Light within the NIR II range (e.g., from 900 to 1700 nm, e.g., from 900 to 1200 nm) can achieve improved tissue penetration (e.g., when mapping nerves through fat).

In some embodiments, imaging apparatus 125 is a functional camera system for mapping (e.g., in 2D or 3D) perfusion, oxygenation status, or other functional parameter in a tissue of patient 135. For example, intrinsic tissue signals can be used themselves or in combination with a probe (e.g., with or without a probe) to obtain information about tissue structures of subject 135. A perfusion measurement based on spectrum output from imaging apparatus 125 can be derived from the spectrum of, for example, oxyhemoglobin or deoxyhemoglobin in the tissue structure of subject 135. For example, the processor may derive real-time 3D functional information [e.g., oxygenation states, e.g., perfusion (flow) status, e.g., determined voxel-by-voxel, or segmented-volume-by-segmented-volume] using NIR light detected at a plurality of wavelengths and/or wavelength bands (e.g., via machine learning based hyperspectral analysis or other algorithms). The processor may then produce a real-time augmented reality (AR) overlay (e.g., 3D representation) using the real-time sensor position information (e.g., from motion tracker and the corresponding tracking sensors) and the real-time 3D functional information. The AR overlay can be produced, for example, by performing an ANN/CNN reconstruction.

C. Dynamic Tracker

As described above, the dynamic motion tracker (e.g., motion tracker 150 of FIG. 1) allows for the dynamic motion tracking of tracking sensors (e.g., fiducial markers during surgery). The 3D locations of these sensors are tracked as a function of time and used in producing (e.g., reconstructing), aligning, and/or orienting a real-time AR overlay (e.g., 3D representation). The dynamic motion tracker may be a commercially available optical tracking system or electromagnetic tracking system (e.g., with no line-of-sight limitations) (e.g., NDI, Polaris Series, and the like). Certain electromagnetic tracking systems allow for consistent and reliable tracking even when individuals and/or equipment pass through the line of site between the motion tracker and one or more of the tracking sensors. The dynamic tracking sensor tracks, in real-time, the location of disposable and/or non-disposable tracking sensors affixed to one or more of (a) the patient, (b) the surgeon's AR headset or other wearable device or electronic display, (c) one or more surgical instruments, (d) a video/NIR camera, and (e) a projector for displaying the AR overlay. For example, the position of a surgical implement (e.g., a surgical catheter inserted into the body of a patient) may be tracked such that a representation of the implement is also presented for view in a rendered AR overlay, e.g., thereby revealing its location within the body of the patient. As depicted in FIG. 1, dynamic tracking system 150 sends signal(s) to the processor for registration of the AR overlay (e.g., to accurately position the overlay with respect to the body of the patient).

D. Electronic Display

Various (e.g., commercially available) electronic displays may be used in the systems and methods described herein for display of a rendered AR overlay. The illustrative example of FIG. 1 shows an embodiment in which the electronic display is a hands-free wearable device 110 (e.g., an optical head-worn, head-mounted display, e.g., Oculus, Hololens, Sony, Vuzix, Google Glass, e.g., a binocular or monocular display). According to this illustrative embodiment, the AR overlay is displayed in surgeon's line-of-sight so that the AR overlay is superimposed in the surgeon's field of view. The hands-free device 110 has disposable or non-disposable sensor(s) 115 affixed thereto which are detectable by the dynamic motion tracker 150 so that location of the device 110 is tracked and the AR overlay is adjusted accordingly in real time (e.g., the position of the headset 110 is tracked in relation to patient/surgical field).

The AR overlay may feature an image of a dual-modality cancer-targeted nanoparticle probe (e.g., positionally mapped in relation to the surgeon's field of view through the hands-free device), and/or structures viewable thereby (e.g., tumor margin contour, nerve tissue, lymph nodes, etc., onto/into which the probe has associated/concentrated). The AR overlay may have gradations of color/intensity or other graphical cues to indicate relative concentrations and/or relative depths of the nanoparticle probe beneath the surface of the patient. The AR overlay may additionally feature tissue structures (e.g., bones, organs, tumor, different tissue types) beneath the viewable surface of the patient (e.g., determined using pre-operative images). The AR overlay may be reconstructed and presented to the surgeon 120 via the hands-free wearable device 110 in 3D perspective such that structures and/or probe regions adjust with movement of the surgeon's head, providing intuitive 3D perspective to the surgeon. This feature, for example, can facilitate improved outcomes of medical procedures by providing a more intuitive visual experience for the surgeon.

The AR overlay, in some embodiments, localizes sentinel and distal lymph nodes (via probes that associate with these structures) to determine best surgical route of entry and approach while limiting dissection of non-diseased/normal tissues. The AR overlay, in some embodiments, localizes tumor margins in relation to surrounding normal tissue and/or identify residual disease at the surgical site to more precisely define sites of disease while limiting resection of normal tissues. The AR overlay, in some embodiments, localizes normal vital tissue structures to minimize risk of injury or damage to those structures during surgical procedures. For example, if used as part of a surgical haptic feedback surgical system, the AR overlay can define "go", "no-go", and/or "slow-go" zones (and/or haptic wells and/or other haptic cues). For example, the haptic cues may physically limit areas in which the surgeon can manipulate surgical tools. In some embodiments, an additional navigation system and/or tracking sensors disposed on the surgical tools may be required to achieve haptic feedback.

Figure 2:
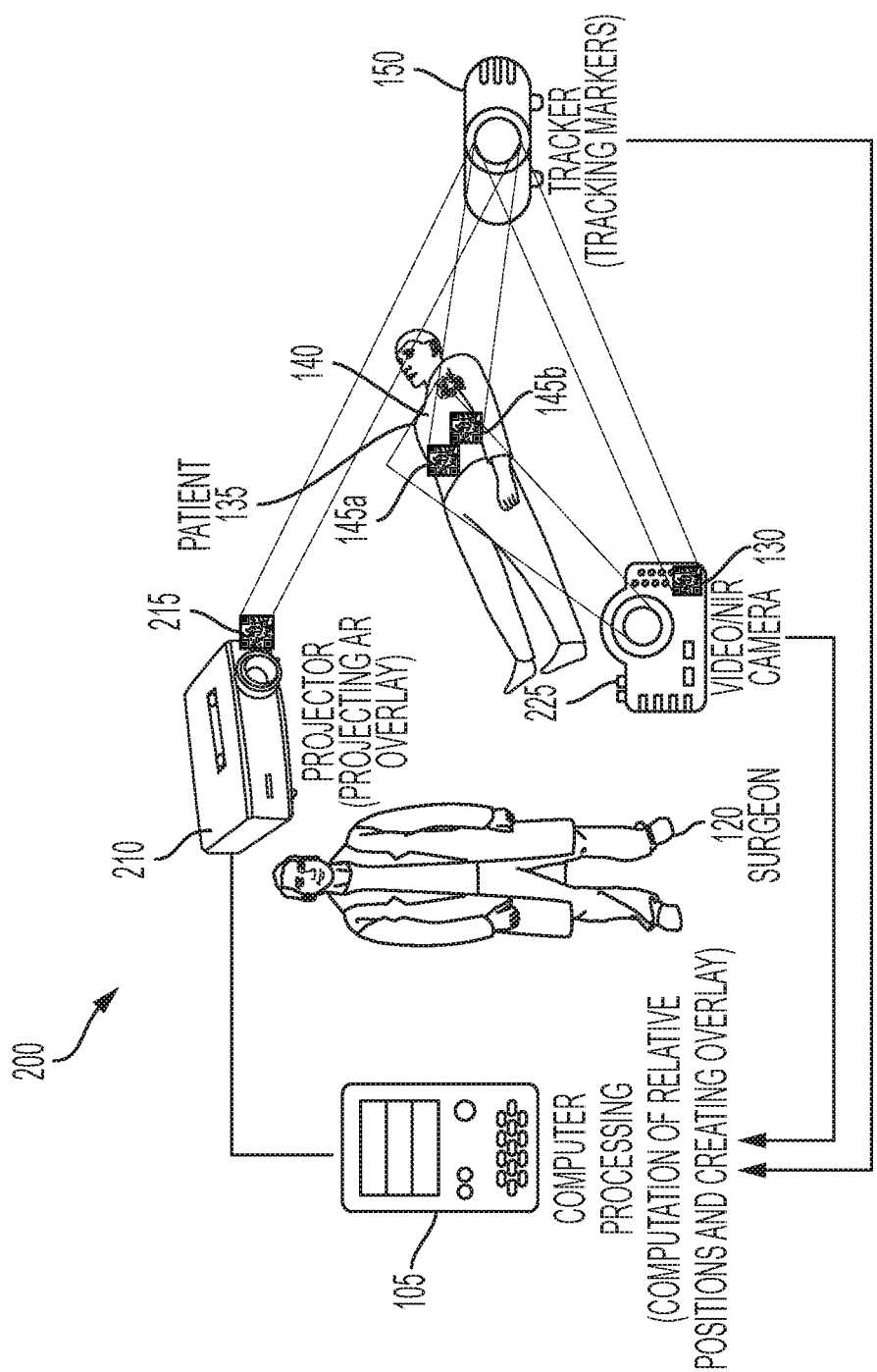
FIG. 2 is a schematic diagram of a system for the rendering and real-time display of an augmented reality overlay representation of one or more probe species in tissue for enhanced real-time visualization of one or more tissue structures of a subject, according to an illustrative embodiment.
Figure 3:
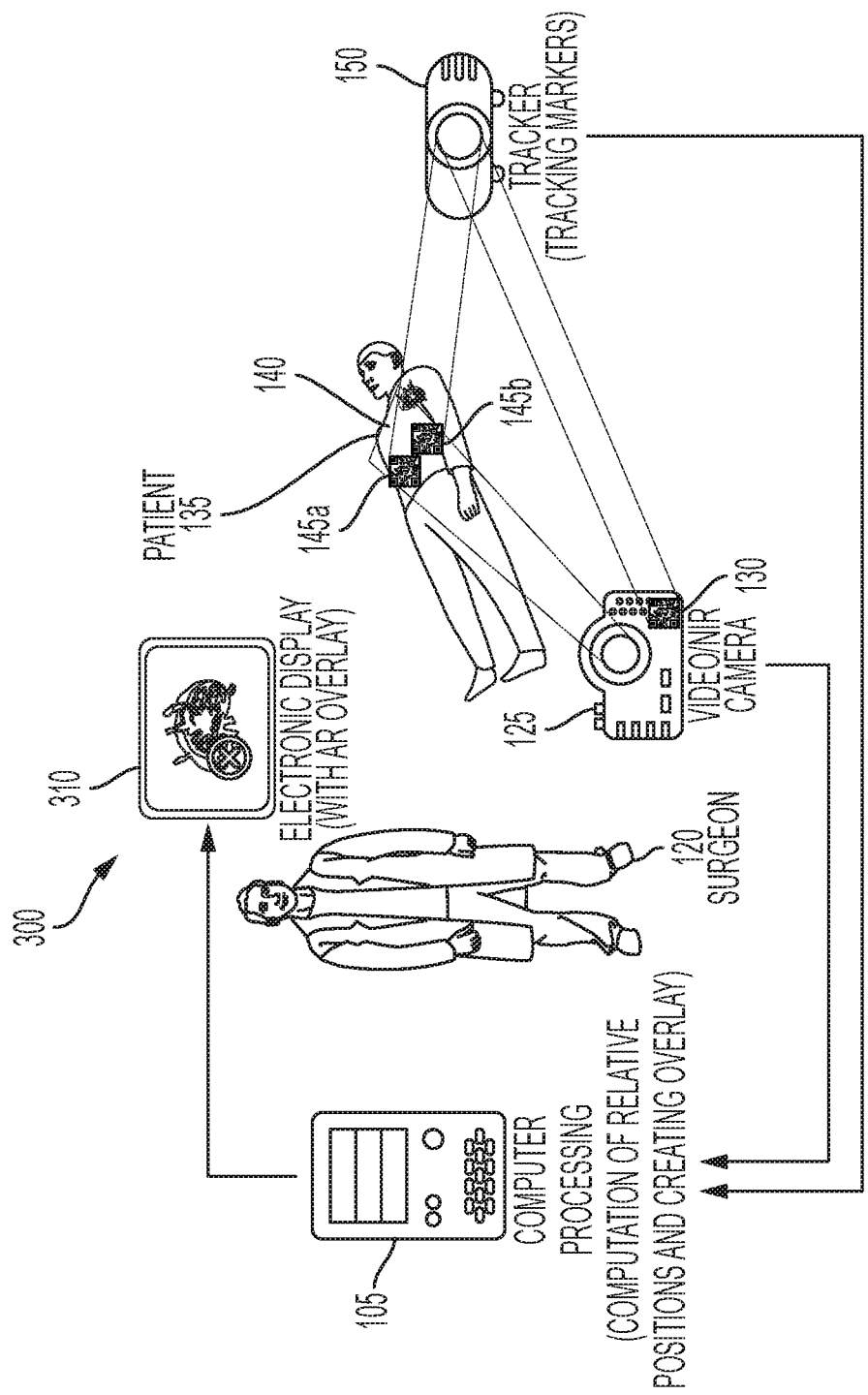
FIG. 3 is a schematic diagram of a system for the rendering and real-time display of an augmented reality overlay representation of one or more dual-modality probe species in tissue for enhanced real-time visualization of one or more tissue structures of a subject, according to an illustrative embodiment.

As shown in the illustrative examples of FIG. 2 and FIG. 3, in some embodiments, the AR overlay is not displayed using a wearable device. For example, as shown in FIG. 2, the AR overlay can be directly projected onto the surgical field using an optical projection system 210. The optical projection system 210 can include tracking sensor(s) 215 or may be positioned in a fixed, known location. Disposable and/or non-disposable sensors are affixed to the patient or otherwise placed in the surgical field for real-time detection by the dynamic motion tracking system 150 and adjustment of the AR overlay, accordingly. The AR overlay may include an image of a dual-modality cancer-targeted nanoparticle probe (e.g., mapped to the viewable surface of the patient), and/or structures viewable thereby (e.g., tumor margin contour, nerve tissue, lymph nodes, etc., onto/into which the probe has associated/concentrated). The AR overlay may have gradations of color/intensity or other graphical cues to indicate relative concentrations and/or relative depths of the nanoparticle probe beneath the viewable surface.

As shown in FIG. 3, the AR overlay may be displayed on a 2D electronic display 310. For example, the 2D display 310 may be an LED or LCD screen, a computer monitor, a tablet computer display, or the like. For example, the AR overlay may be presented on a traditional 2D display 310 superimposed on a real-time video image of the surgical field (or a portion thereof). The AR overlay may include a rendering of the real-time location of one or more dual-modality probes, and, optionally, a representation of functional parameters associated with the tissue (e.g., perfusion, e.g., oxygenation states).

Figure 6:
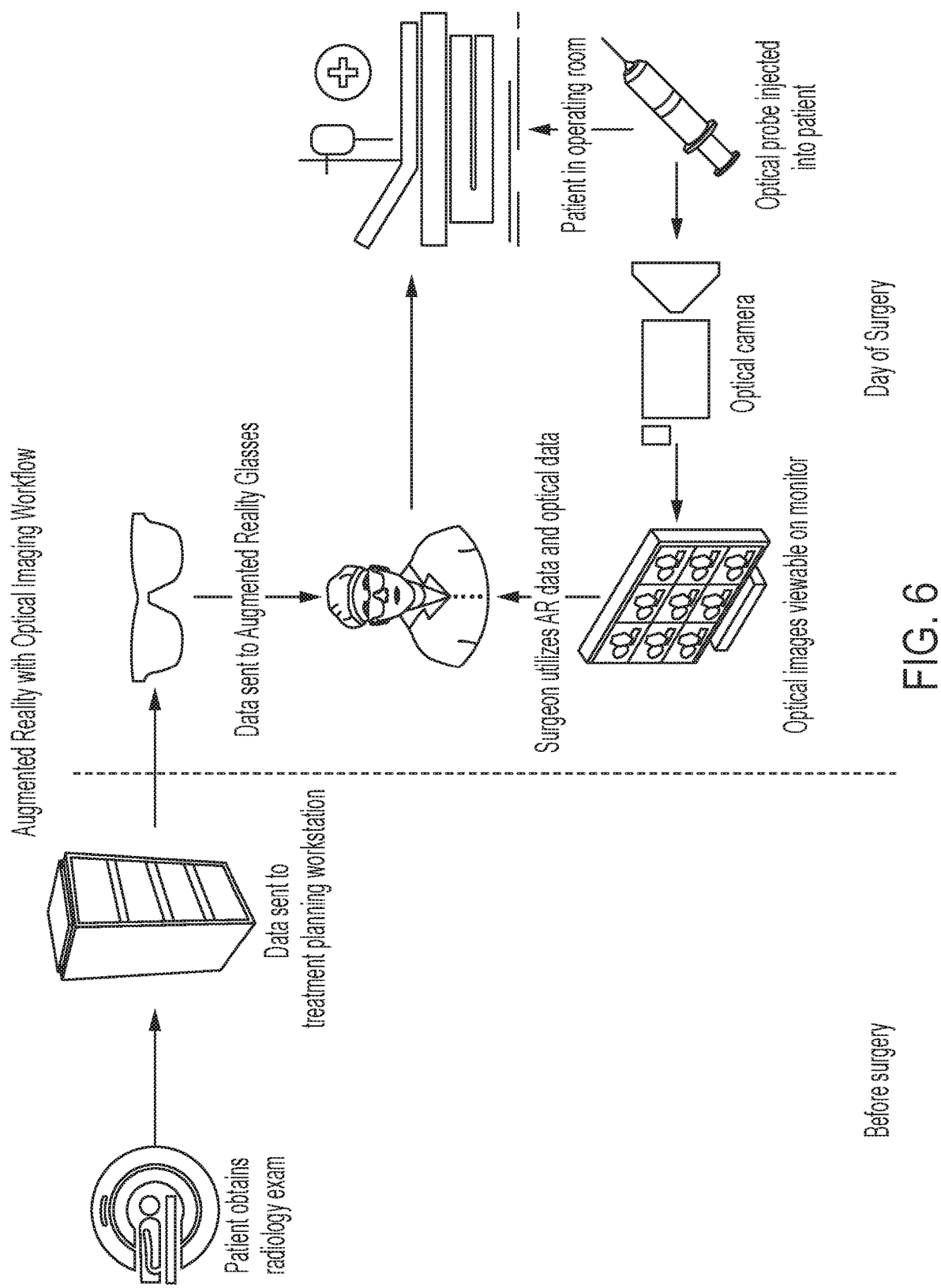
FIG. 6 is a schematic representation of a method for the rendering and real-time display of an augmented reality overlay representation of one or more probe species in tissue for enhanced real-time visualization of one or more tissue structures of a subject, according to an illustrative embodiment.

FIG. 6 shows a schematic diagram of a method for the rendering and real-time display of an augmented reality overlay representation of one or more probe species in tissue for enhanced real-time visualization of one or more tissue structures of a subject, according to an illustrative embodiment. In this embodiment, a subject (patient) obtains a radiology exam, and data is sent to a treatment planning workstation before surgery. On the day of surgery, data from the workstation is sent to augmented reality glasses, which a surgeon wears while the subject (patient) is in the operating room. An optical probe is administered to the subject (patient). An optical camera detects one or more signals emitted by the probe species. The optical camera processes the received signals to generate one or more images viewable on a monitor and/or the augmented reality glasses. For example, an augmented reality overlay comprising the radiological and optical images is generated and displayed to the surgeon via the augmented reality glasses. The overlay provides enhanced real-time visualization of one or more tissue structures of the subject (patient) to assist the surgeon during the procedure. For example, where the administered probe concentrates in nerve tissue (or other healthy tissue types) the overlay may allow a cancer surgeon to avoid cutting tissue corresponding to the nerve or other healthy tissue types. Also, for example, where the administered probe accumulates in tumor cells/tumor tissue, the overlay may allow a cancer surgeon to better visualize tumor margins so that more healthy tissue can be preserved and so that more of the cancer tissue can be removed. Moreover, for example, the overlay may allow a doctor to plan or guide other treatments, e.g., post-surgery, such as radiation therapy, to enhance effectiveness of such therapy and/or reduce negative side effects (e.g., deliver radiation to locations that maximize effectiveness and minimize side effects of the radiation).

In some embodiments, the described systems and methods are used for a clinical procedure rather than a procedure conducted in an operating room.

E. Computer Processing

AI-assisted creation of AR overlay and/or registration of AR overlay may be achieved using artificial neural networks (ANNs) to process image streams. An AR overlay may include 3D graphical representation of a probe [e.g., a dual-modality (PET-optical) cancer-targeting nanoparticle probe], imaged via PET or other system for detection of radiolabels [e.g., imaged prior to surgery (pre-operatively), perioperative, or intraoperatively]. An AR overlay may also or alternatively include graphical representation of 3D anatomical structures (e.g., from CT and/or MRI image(s)).

Prior to surgery (or at the beginning of a surgical procedure), PET or SPECT (or other functional imaging), can be performed for radiodetection of the dual-modality probe and detailed 3D mapping of the probe (e.g., optionally combined with 3D anatomical imaging, e.g., CT or MRI). A 3D surgical site model is thus created by the processor for graphically representing the presence of the probe in the patient and/or the tissue structures of the patient. Referring again to the illustrative example of FIG. 1, the 3D surgical site model is updated in real time by the processor (e.g., of computer 105) based on signals from the dynamic motion tracker 150, which tracks the location of fiducial sensors 145a,b in/on (or otherwise fixed in relation to) the patient and, in some embodiments, tracks fiducial sensors 115 affixed to the hands-free wearable device. 3D image reconstruction and positional registration is performed by the processor to present a visual representation of the 3D surgical site model to the surgeon 120 via the hands-fee wearable device 110.

In some embodiments, a real-time detected fluorescent signal serves as a 3D "fiducial" for registration of the AR overlay within a surgeon's line of sight (via the electronic display). Referring again to the illustrative example of FIG. 1, a sensor 125 in the operating room (e.g., mounted for intraoperative fluorescent imaging of the surgical site) detects fluorescence emitted by the dual-modality probe (e.g., nanoparticles or non-particle probe) during surgery when such fluorescence is detectable [e.g., when the nanoparticles are at or just beneath (e.g., within several centimeters from the surface of the patient's skin) the exposed surface of the patient tissue]. The AR overlay can then be adjusted (e.g., positionally), and/or the 3D tissue structures graphically represented in the AR overlay can be adjusted, in real time based at least in part on the detected fluorescence. This may help reduce or obviate the need for extensive pre-operative or perioperative imaging of the patient, which may otherwise be required for proper registration in surgical AR systems.

Embodiments of the systems and methods described herein may use the components described above without necessarily requiring: (i) the in-operating-room Video/NIR camera (e.g., NIR imaging apparatus 125 of FIGS. 1-3), and (ii) the dynamic tracker (e.g., dynamic motion tracker 150 of FIGS. 1-3).

Figure 4:
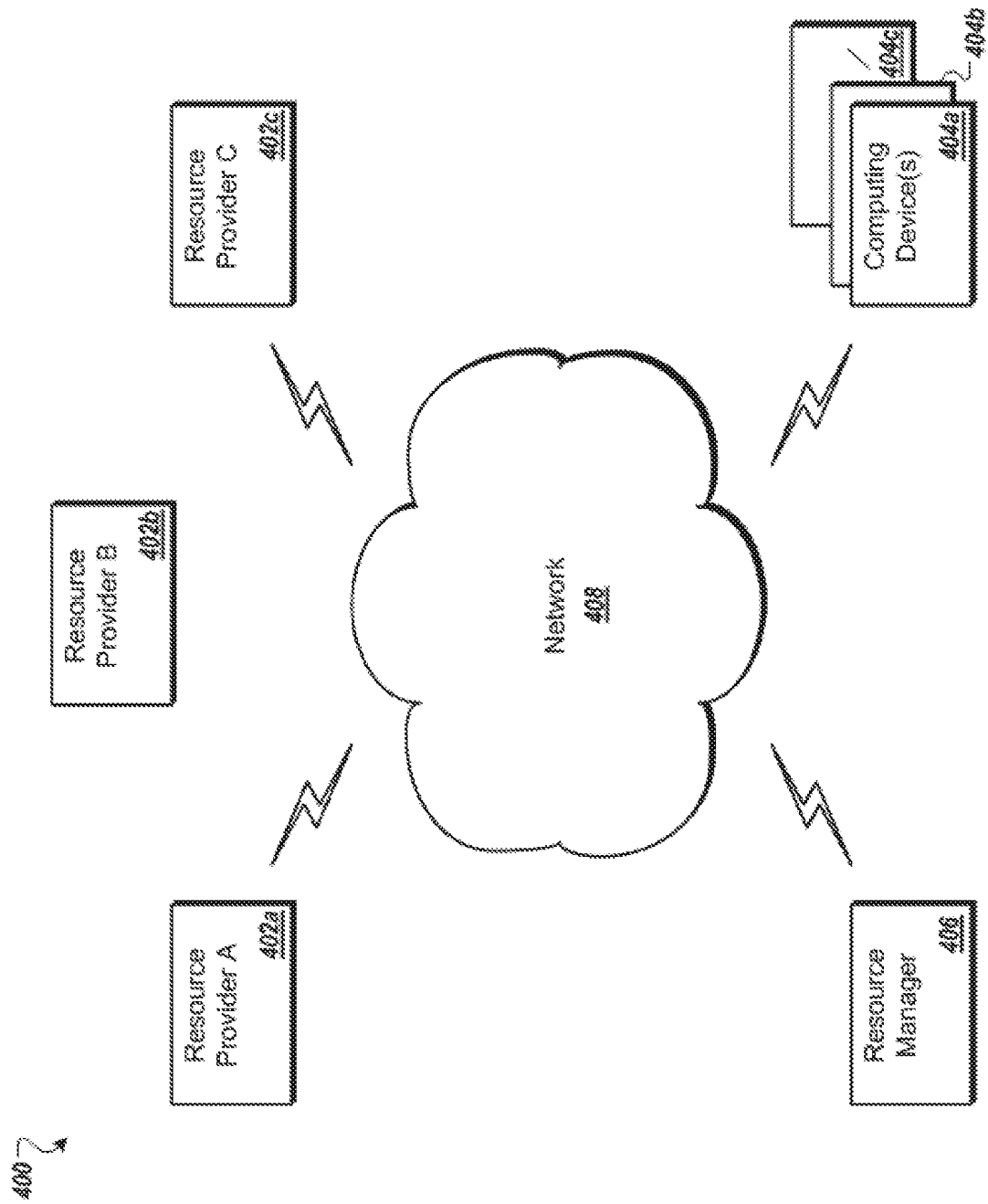
FIG. 4 is a block diagram of an example network environment for use in the methods and systems described herein, according to an illustrative embodiment.
Figure 5:
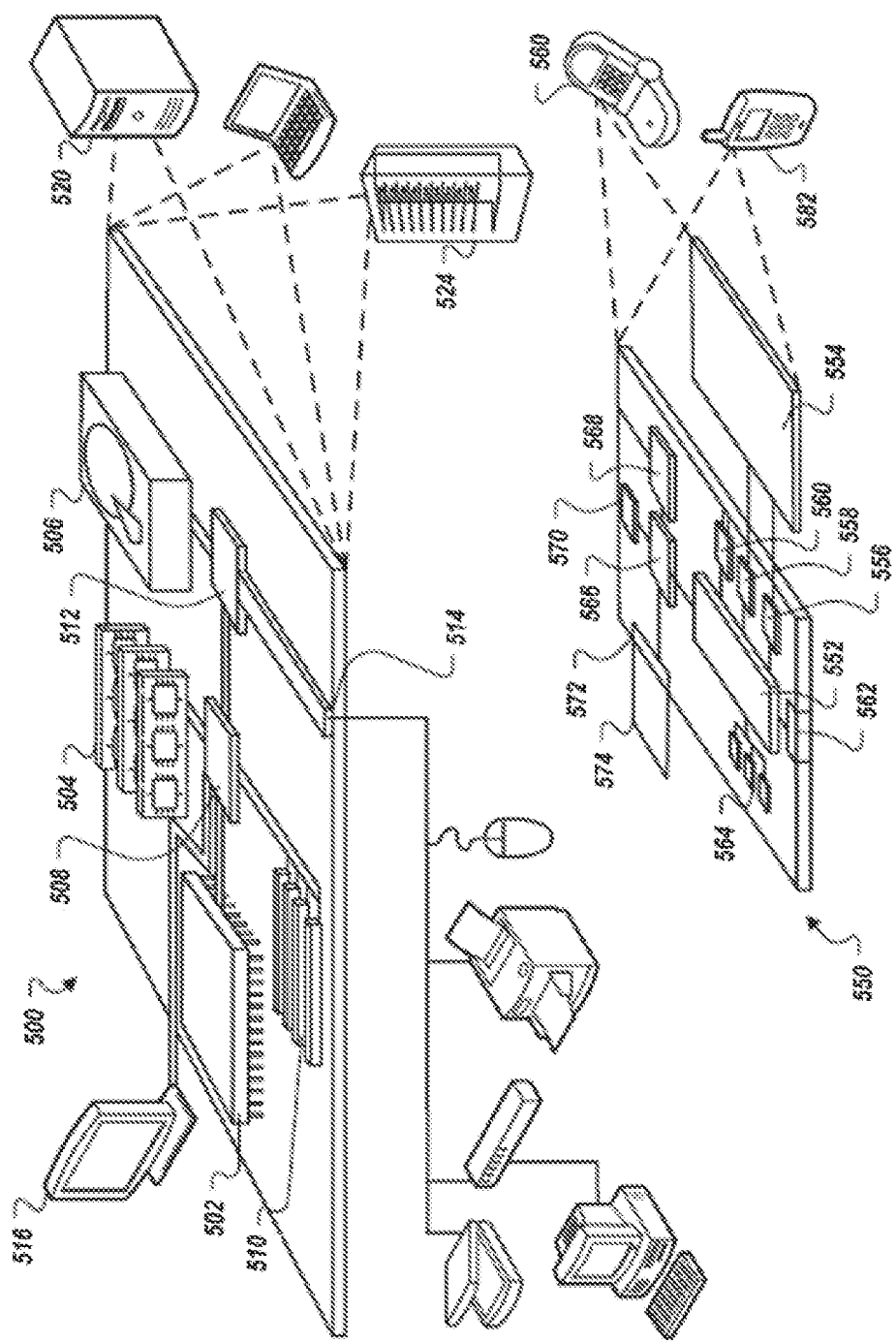
FIG. 5 is a block diagram of an example computing device and an example mobile computing device, for use in illustrative embodiment.

Illustrative examples of computer and network implementations for use in various embodiments of the systems and methods for the rendering and real-time display of an augmented reality overlay representation of one or more probe species in tissue for enhanced real-time visualization of one or more tissue structures of a subject are shown in FIG. 4 and FIG. 5 below.

As shown in FIG. 4, an implementation of a network environment 400 for use in the systems, methods, and architectures described herein, is shown and described. In brief overview, referring now to FIG. 4, a block diagram of an exemplary cloud computing environment 400 is shown and described. The cloud computing environment 400 may include one or more resource providers 402a, 402b, 402c (collectively, 402). Each resource provider 402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 402 may be connected to any other resource provider 402 in the cloud computing environment 400. In some implementations, the resource providers 402 may be connected over a computer network 408. Each resource provider 402 may be connected to one or more computing device 404a, 404b, 404c (collectively, 404), over the computer network 408.

The cloud computing environment 400 may include a resource manager 406. The resource manager 406 may be connected to the resource providers 402 and the computing devices 404 over the computer network 408. In some implementations, the resource manager 406 may facilitate the provision of computing resources by one or more resource providers 402 to one or more computing devices 404. The resource manager 406 may receive a request for a computing resource from a particular computing device 404. The resource manager 406 may identify one or more resource providers 402 capable of providing the computing resource requested by the computing device 404. The resource manager 406 may select a resource provider 402 to provide the computing resource. The resource manager 406 may facilitate a connection between the resource provider 402 and a particular computing device 404. In some implementations, the resource manager 406 may establish a connection between a particular resource provider 402 and a particular computing device 404. In some implementations, the resource manager 406 may redirect a particular computing device 404 to a particular resource provider 402 with the requested computing resource.

FIG. 5 shows an example of a computing device 500 and a mobile computing device 550 that can be used in the methods and systems described in this disclosure. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 500 includes a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 manages bandwidth-intensive operations for the computing device 500, while the low-speed interface 512 manages lower bandwidth-intensive operations. Such allocation of functions is an example only. In some implementations, the high-speed interface 508 is coupled to the memory 504, the display 516 (e.g., through a graphics processor or accelerator), and to the high-speed expansion ports 510, which may accept various expansion cards (not shown). In the implementation, the low-speed interface 512 is coupled to the storage device 506 and the low-speed expansion port 514. The low-speed expansion port 514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 includes a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, a SIMM (Single In Line Memory Module) card interface or a DIMM (Double In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provided as a security module for the mobile computing device 550, and may be programmed with instructions that permit secure use of the mobile computing device 550. In addition, secure applications may be provided via the DIMM cards, along with additional information, such as placing identifying information on the DIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 550 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a Bluetooth®, Wi-Fi™, or other such transceiver (not shown). In addition, a GPS (Global Positioning System) receiver module 570 may provide additional navigation- and location-related wireless data to the mobile computing device 550, which may be used as appropriate by applications running on the mobile computing device 550.

The mobile computing device 550 may also communicate audibly using an audio codec 560, which may receive spoken information from a user and convert it to usable digital information. The audio codec 560 may likewise generate audible sound for a user, such as through a speaker, e.g., in a handset of the mobile computing device 550. Such sound may include sound from voice telephone calls, may include recorded sound (e.g., voice messages, music files, etc.) and may also include sound generated by applications operating on the mobile computing device 550.

The mobile computing device 550 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A system for the rendering and real-time display of an augmented reality (AR) overlay representation of one or more dual-modality probe species in tissue for enhanced real-time visualization of one or more tissue structures of a subject, the system comprising:
    a dynamic motion tracker for detecting tracking sensors and for producing real-time sensor position information; and
    a real-time near-infrared (NIR) imaging apparatus for (A) detecting in real-time NIR light (i) at each of one or more discrete wavelengths and/or (ii) over each of one or more discrete wavelength bands and (B) obtaining in real-time one or more series of NIR images; and
    a processor and a memory having instructions stored thereon, wherein the instructions, when executed by the processor, cause the processor to:
        receive and/or store in real-time one or more radiological images representing emission of one or more radiolabel species of the one or more dual-modality probe species having been administered to the subject;
        receive in real-time the one or more series of NIR images obtained by the real-time NIR imaging apparatus, each series corresponding to an emission frequency of one of the one or more dual-modality probe species; and
        produce in real-time the real-time AR overlay using the one or more radiological images, the one or more series of real-time NIR images, and the real-time sensor position information.

2. The system of claim 1, wherein the tracking sensors are placed on/in/around the subject and/or the tracking sensors are placed on a hands-free wearable device.

3. The system of claim 1, wherein the one or more radiological images comprises a time-series of 3D images.

4. The system of claim 1, further comprising an electronic display for display of the AR overlay superimposed on a view of the subject.

5. The system of claim 4, wherein the electronic display is a hands-free wearable device.

6. The system of claim 4, wherein the AR overlay is superimposed on a view of an operating field as viewed by a surgeon, updated in real time.

7. A kit comprising the system of claim 1 and the one or more dual-modality probe species.

8. The system of claim 1, wherein the one or more dual-modality probe species comprise fluorescent silica nanoparticles.

9. A system for the rendering and real-time display of an augmented reality (AR) overlay representation of 3D functional information derived from intrinsic tissue signals for enhanced real-time visualization of one or more tissue structures of a subject, the system comprising:
    a dynamic motion tracker for detecting tracking sensors and for producing real-time sensor position information;
    a real-time near-infrared (NIR) imaging apparatus for (A) detecting in real-time NIR light (i) at each of one or more discrete wavelengths and/or (ii) over each of one or more discrete wavelength bands and (B) obtaining in real-time one or more series of NIR images; and
    a processor and a memory having instructions stored thereon, wherein the instructions, when executed by the processor, cause the processor to:
        derive in real-time, real-time 3D functional information using the detected NIR light at the plurality of wavelengths and/or wavelength bands;
        receive in real-time the one or more series of NIR images obtained by the real-time NIR imaging apparatus, each series corresponding to an emission frequency of one of the one or more dual-modality probe species; and
        produce, in real-time, the real-time AR overlay using the real-time sensor position information, the one or more series of real-time NIR images, and the real-time 3D functional information.

10. The system of claim 9, wherein the tracking sensors are placed on/in/around the subject and/or the tracking sensors are placed on a hands-free wearable device.

11. The system of claim 9, wherein each of the plurality of discrete wavelengths and/or wavelength bands are within a range from 400 nm to 2500 nm.

12. The system of claim 9, wherein the real-time 3D functional information is an oxygenation state.

13. A method for the rendering and real-time display of a real-time augmented reality (AR) overlay representation of 3D functional information derived from intrinsic tissue signals for enhanced real-time visualization of one or more tissue structures of a subject, the method comprising:
   detecting in real-time tracking sensors and producing real-time sensor position information via a dynamic motion tracker;
   detecting in real-time near-infrared (NIR) light (i) at each of a plurality of discrete wavelengths and/or (ii) over each of a plurality of discrete wavelength bands, via a real-time NIR imaging apparatus, and obtaining in real-time one or more series of NIR images;
   computing in real-time, by a processor of a computing device, real-time 3D functional information using the detected NIR light at the plurality of wavelengths and/or wavelength bands, and the one or more series of real-time NIR images; and
   producing in real-time, by the processor, the real-time AR overlay using the real-time sensor position information, the one or more series of real-time NIR images, and the real-time 3D functional information.

14. A system for the rendering and real-time display of an augmented reality (AR) overlay representation of one or more probe species in tissue for enhanced real-time visualization of one or more tissue structures of a subject, the system comprising:
   a dynamic motion tracker for detecting tracking sensors and for producing real-time sensor position information;
   a real-time near-infrared (NIR) imaging apparatus for (A) detecting in real-time NIR light (i) at each of one or more discrete wavelengths and/or (ii) over each of one or more discrete wavelength bands and (B) obtaining in real-time one or more series of NIR images; and
   a processor and a memory having instructions stored thereon, wherein the instructions, when executed by the processor, cause the processor to:
      receive and/or store one or more structural images of the subject;
      receive in real-time the one or more series of NIR images obtained by the real-time NIR imaging apparatus, each series corresponding to an emission frequency of one of the one or more dual-modality probe species; and
      produce in real-time the real-time AR overlay using the one or more structural images of the subject, the one or more series of NIR images, and the real-time sensor position information.

15. The system of claim 14, wherein the one or more probe species comprise fluorescent silica nanoparticles.

16. The system of claim 14, wherein the instructions, when executed by the processor, cause the processor to render the AR overlay for display, and to update the real-time AR overlay in real-time.

17. The system of claim 14, wherein the tracking sensors are placed on/in/around the subject and/or the tracking sensors are placed on a hands-free wearable device.

18. The system of claim 14, further comprising an electronic display for display of the AR overlay superimposed on a view of the subject.

19. The system of claim 18, wherein the AR overlay is superimposed on a view of an operating field as viewed by a surgeon, updated in real time.

20. A kit comprising the system of claim 14 and the one or more probe species.

* * * * *